United States Patent [19]
Chan

[11] Patent Number: 5,935,169
[45] Date of Patent: Aug. 10, 1999

[54] BONE CEMENT PLUG FOR DEPLOYMENT IN A BONE CANAL

[76] Inventor: Kwan-Ho Chan, 4803 First Pl., Lubbock, Tex. 79416

[21] Appl. No.: 08/800,928

[22] Filed: Feb. 13, 1997

[51] Int. Cl.[6] ..................................................... A61F 2/28
[52] U.S. Cl. ................................ 623/16; 606/62; 606/95; 411/55; 411/60
[58] Field of Search .................................. 623/16, 17, 22, 623/23; 606/60–93, 95; 411/55, 60, 63, 64, 72, 178

[56] References Cited

U.S. PATENT DOCUMENTS

| | | | |
|---|---|---|---|
| 4,011,602 | 3/1977 | Rybicki et al. | 3/1.9 |
| 4,013,071 | 3/1977 | Rosenberg | 623/16 |
| 4,231,120 | 11/1980 | Day | 623/16 |
| 4,245,359 | 1/1981 | Stuhmer | 3/1.9 |
| 4,276,659 | 7/1981 | Hardinge | 3/1.9 |
| 4,293,962 | 10/1981 | Fuson | 3/1.9 |
| 4,302,855 | 12/1981 | Swanson | 3/1.9 |
| 4,344,190 | 8/1982 | Lee et al. | 3/1.9 |
| 4,447,915 | 5/1984 | Weber | 606/95 |
| 4,516,885 | 5/1985 | Calandra, Jr. | 411/60 |
| 4,523,587 | 6/1985 | Frey | 128/92 C |
| 4,627,434 | 12/1986 | Murray | 128/303 R |
| 4,686,973 | 8/1987 | Frisch | 128/92 YZ |
| 4,697,584 | 10/1987 | Haynes | 128/92 VQ |
| 4,745,914 | 5/1988 | Frey et al. | 128/92 VP |
| 4,753,405 | 6/1988 | Camilleri | 411/60 |
| 4,878,791 | 11/1989 | Kurihara et al. | 411/55 |
| 4,904,267 | 2/1990 | Bruce et al. | 623/23 |
| 4,936,859 | 6/1990 | Morscher et al. | 623/18 |
| 4,950,295 | 8/1990 | Weigum et al. | 623/16 |
| 4,994,085 | 2/1991 | Sawai et al. | 623/23 |

(List continued on next page.)

FOREIGN PATENT DOCUMENTS

| | | |
|---|---|---|
| 0006408 | of 1978 | European Pat. Off. . |
| 2253564 | of 1992 | United Kingdom . |
| WO 9415544 | 7/1994 | WIPO . |

OTHER PUBLICATIONS

Paul et al., "A New Femoral Cement Restrictor", The Journal of Arthroplasty, vol. 7, Supplement 1992, pp. 411–413.
"Polyethylene medullary plug according to Stuhmer/Weber", Allo–Pro, Ref. No. 1688 d/e/f—Ed. Dec. 1990.
Artisan™ Bone Plug. Crafted to resist "blowout.", Howmedica, Inc., Rutherford, NJ, 1996, 1 page.
"Artisan™ Bone Plug Crafted for a more secure fit", Howmedica, Inc., Rutherford, NJ, 1996, 4 pages.

*Primary Examiner*—Mickey Yu
*Assistant Examiner*—Tram A. Nguyen
*Attorney, Agent, or Firm*—Pandiscio & Pandiscio

[57] ABSTRACT

A bone cement plug for use in conjunction with bone cement dispensers to compact bone cement into bone canals during total joint replacement surgeries. The bone cement plug includes a core including a substantially cylindrically-shaped base portion defining a threaded bore therein extending axially and distally from a proximal end of the base portion; a first leg portion depending from and extending distally from the base portion; and a second leg portion depending from and extending distally from the base portion and opposed to the first leg portion; the base portion threaded bore being adapted to receive an expander screw to wedge apart the first and second leg portions, whereby to expand the core widthwise to secure the plug in the bone canal; and the expander screw, the screw comprising a generally cylindrically-shaped body having a tapered distal end, and a proximal end in which is disposed a threaded bore, external threads disposed on the body, and an annular flange extending outwardly from the proximal end of the body, the screw being threadedly engageable with the core threaded bore for advancement of the screw into the plug for the wedging apart of the first and second legs. A method is also disclosed for using the bone cement plug to compact bone cement into a bone canal during total joint replacement surgeries.

32 Claims, 17 Drawing Sheets

U.S. PATENT DOCUMENTS

| | | | |
|---|---|---|---|
| 5,061,287 | 10/1991 | Feiler | 623/16 |
| 5,078,746 | 1/1992 | Garner | 623/16 |
| 5,092,891 | 3/1992 | Kummer et al. | 623/16 |
| 5,116,337 | 5/1992 | Johnson | 411/178 |
| 5,145,301 | 9/1992 | Yamamoto | 411/60 |
| 5,360,450 | 11/1994 | Giannini | 623/16 |
| 5,376,120 | 12/1994 | Sarver et al. | 623/16 |
| 5,383,932 | 1/1995 | Wilson et al. | 623/16 |
| 5,496,326 | 3/1996 | Johnson | 606/88 |
| 5,554,191 | 9/1996 | Lahille et al. | 623/17 |
| 5,662,657 | 9/1997 | Carn | 606/95 |
| 5,766,178 | 6/1998 | Michielli et al. | 606/95 |
| 5,782,917 | 7/1998 | Carn | 623/16 |

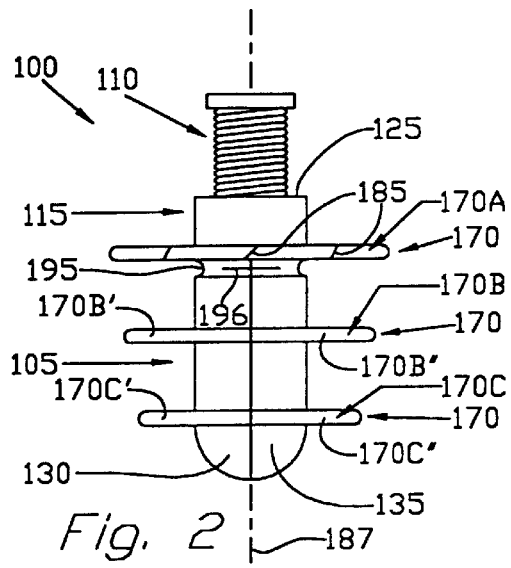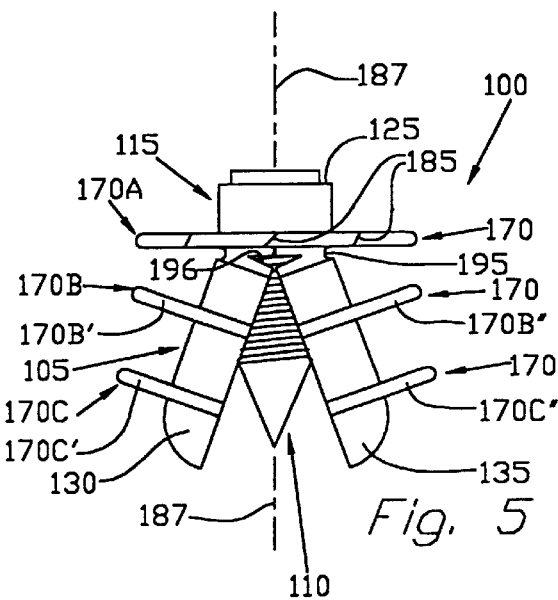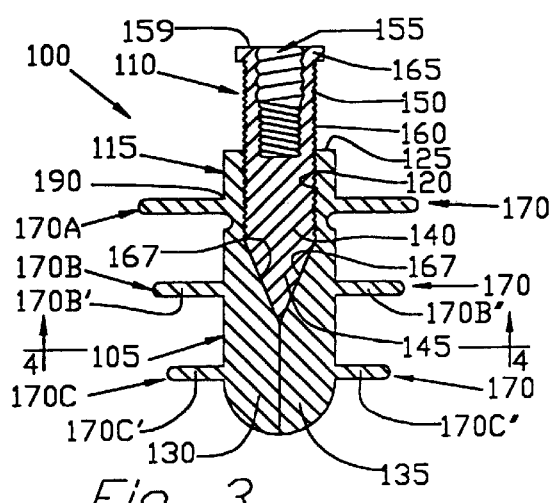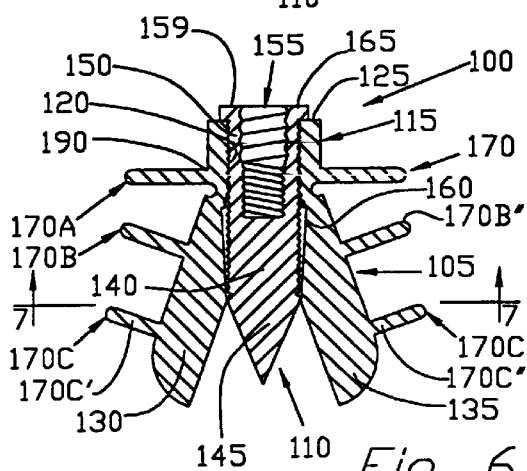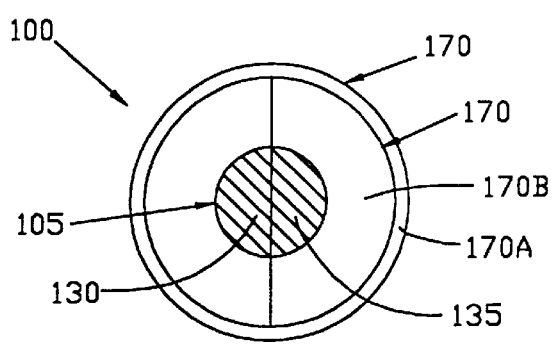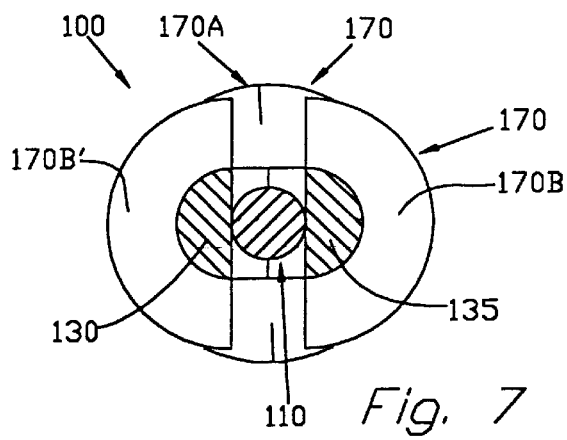

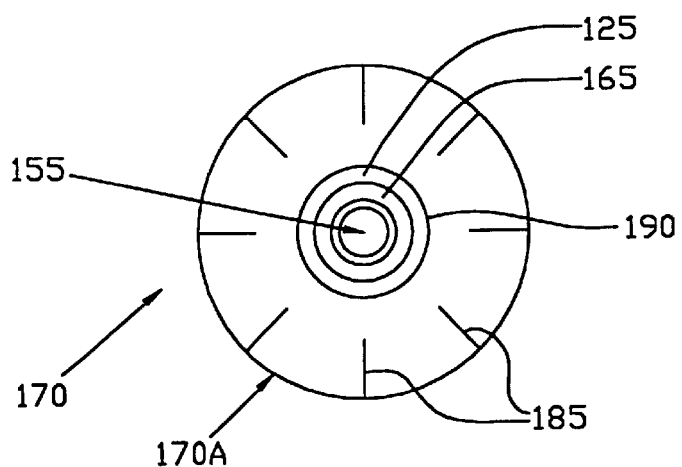
Fig. 8
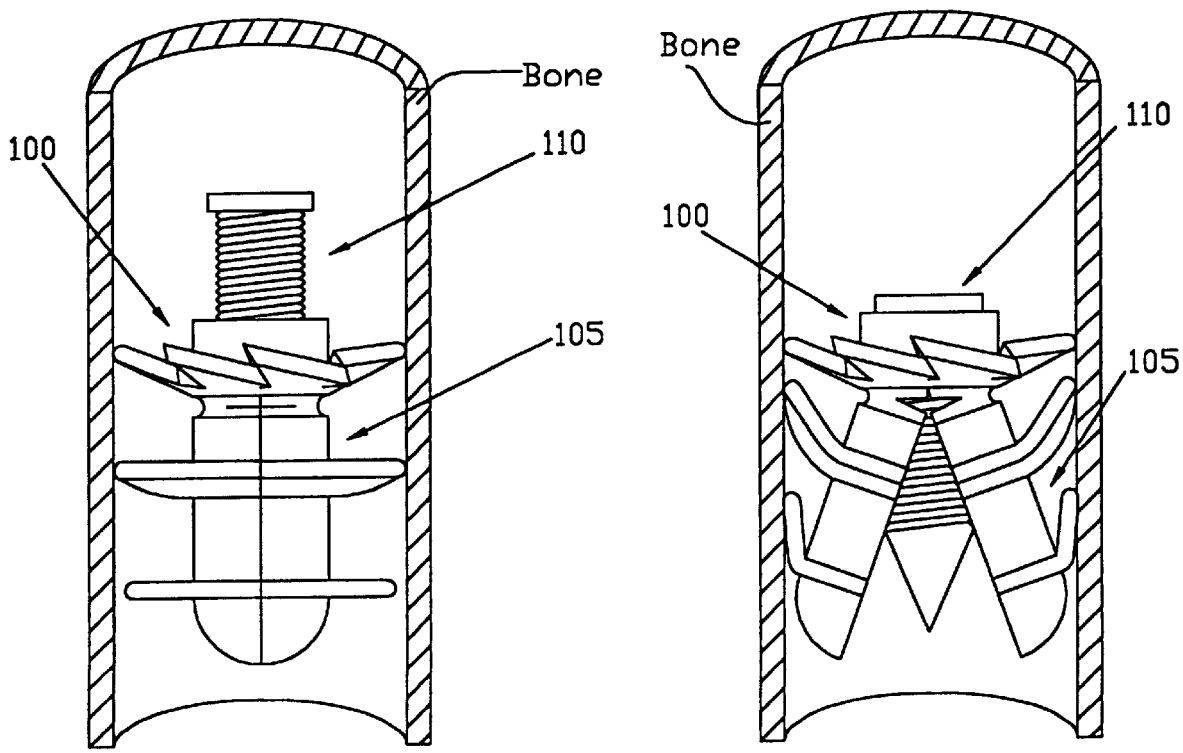
Fig. 9
Fig. 10

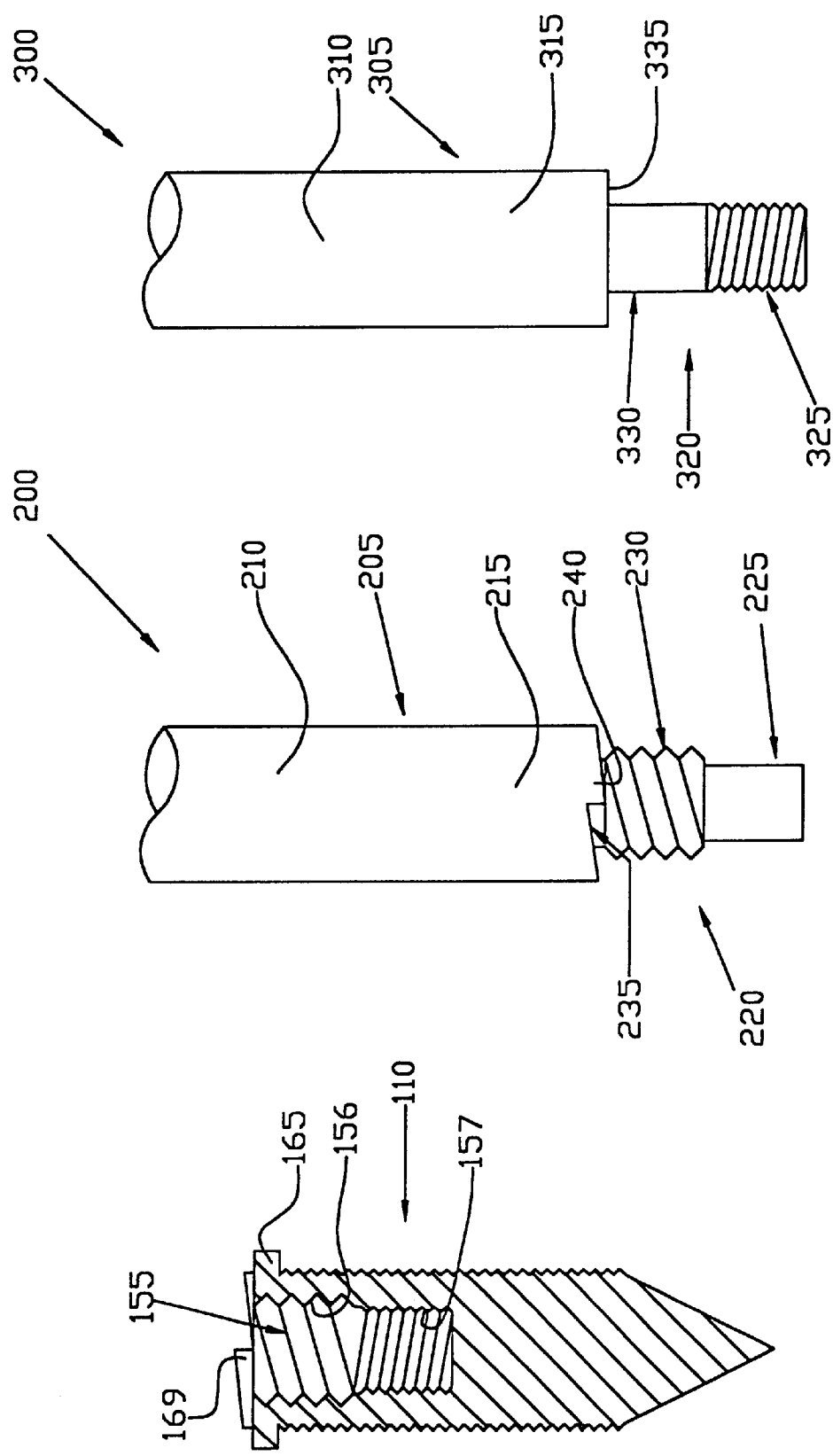

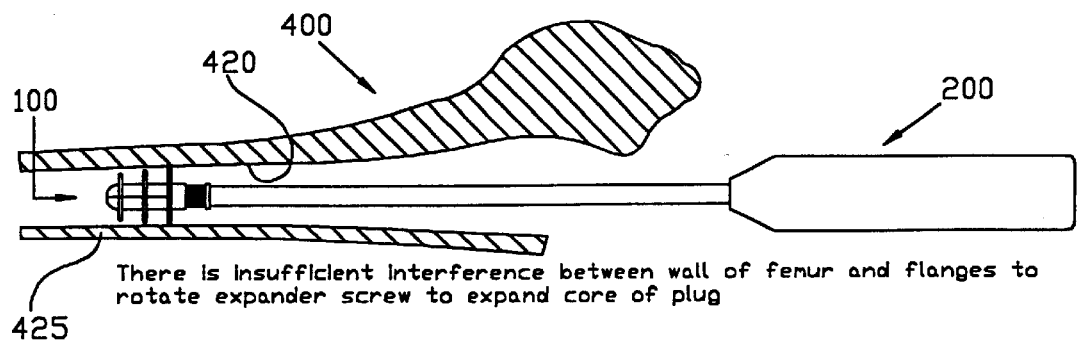

There is insufficient interference between wall of femur and flanges to rotate expander screw to expand core of plug

Fig. 24

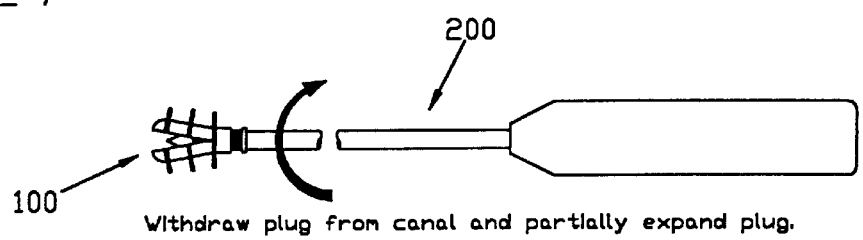

Withdraw plug from canal and partially expand plug.

Fig. 25

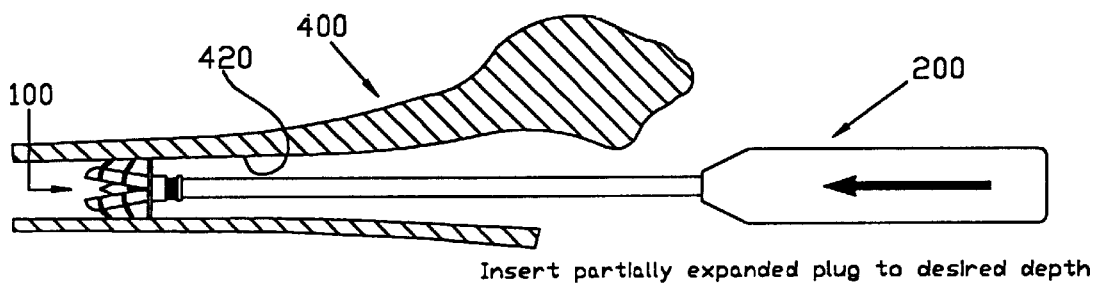

Insert partially expanded plug to desired depth

Fig. 26

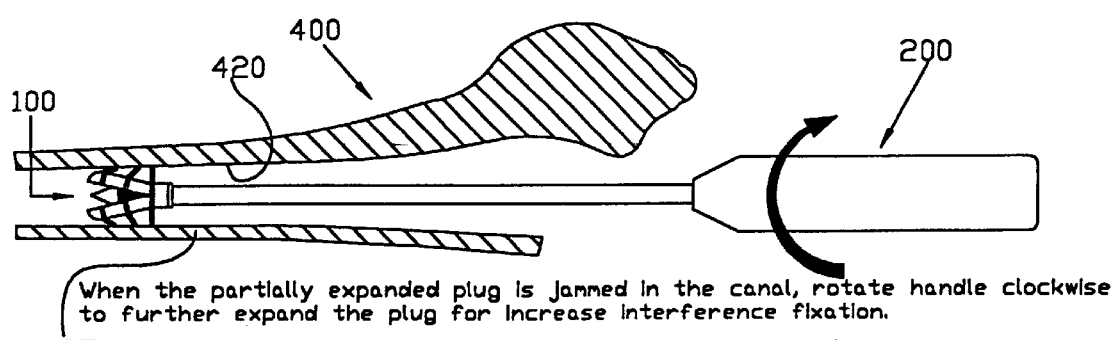

When the partially expanded plug is jammed in the canal, rotate handle clockwise to further expand the plug for increase interference fixation.

Fig. 27

Insert Extractor tip into Expander Screw

Rotate Extractor anticlockwise till it is fully engaged to the Expander Screw

Continue to rotate Extractor anticlockwise to partially back out the Expander Screw allowing the core of the Plug to collapse Pull Plug out of the femoral canal

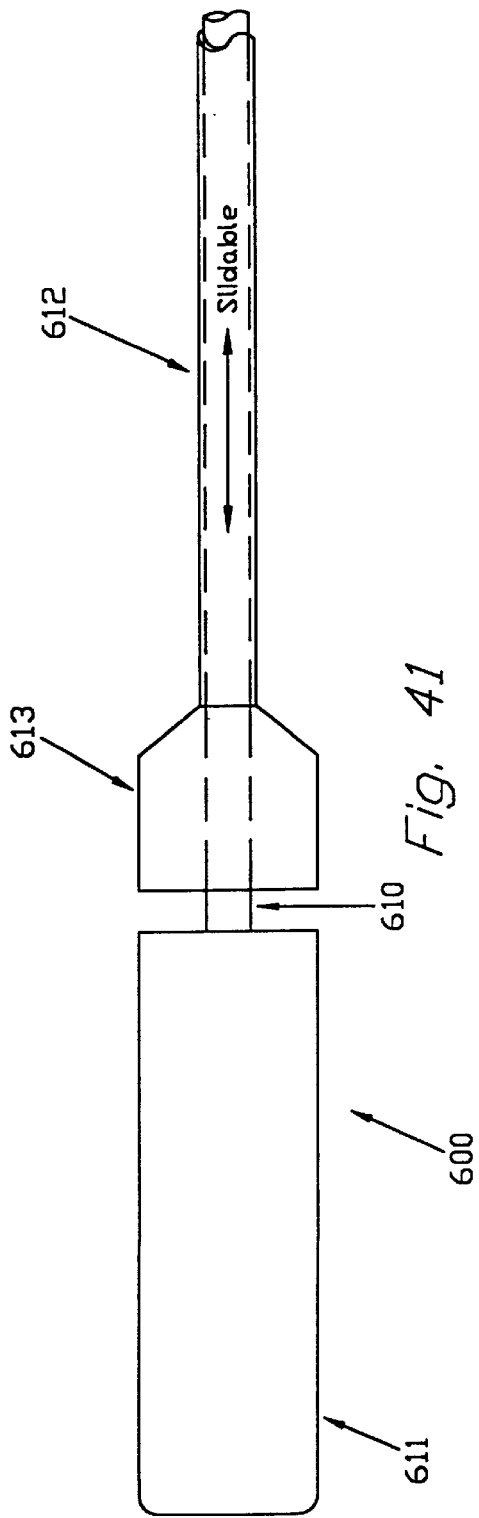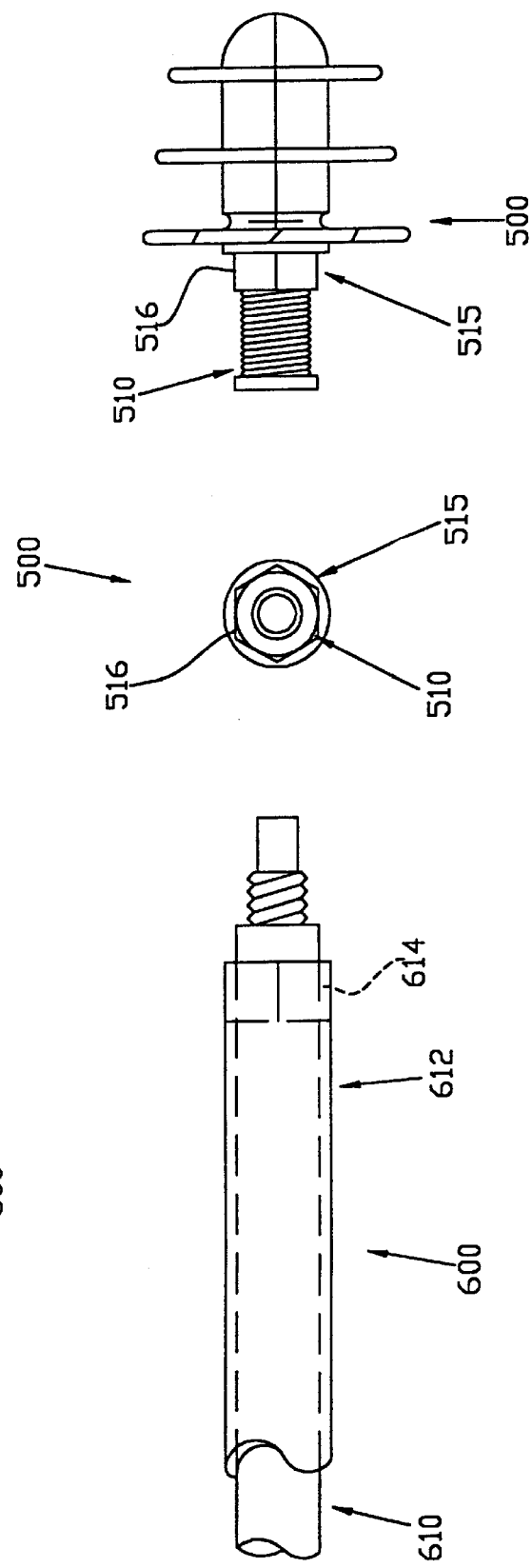
Fig. 41
Fig. 42

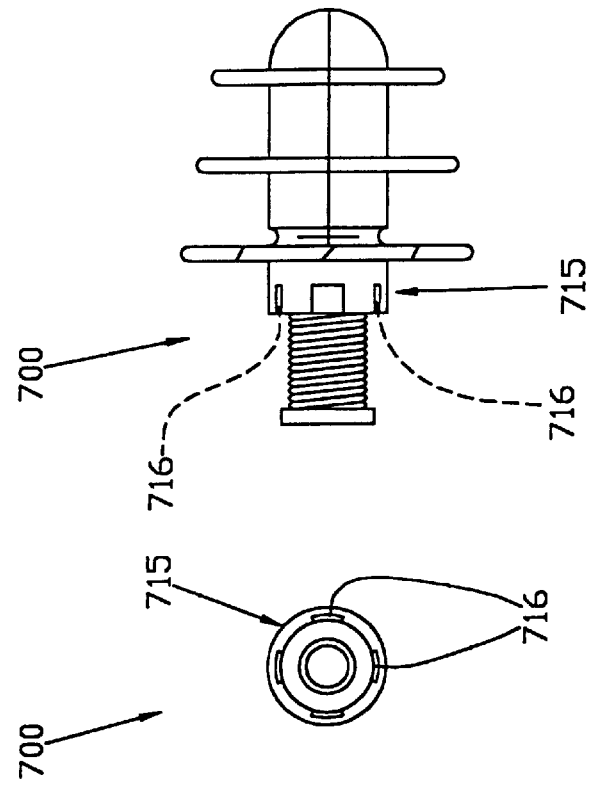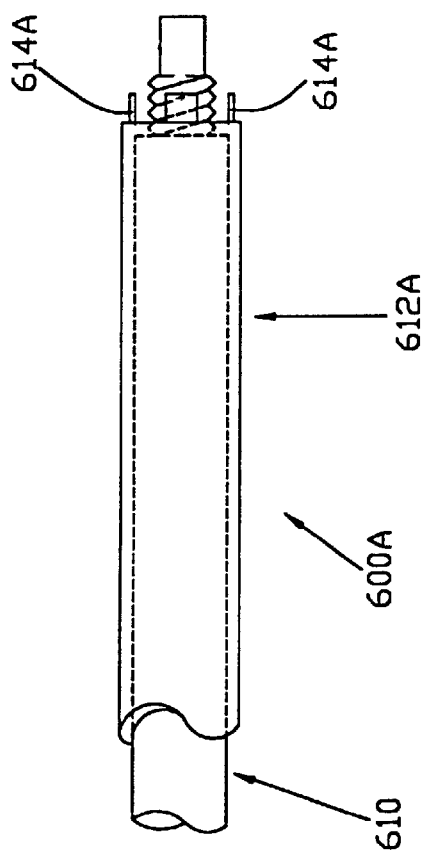
Fig. 49

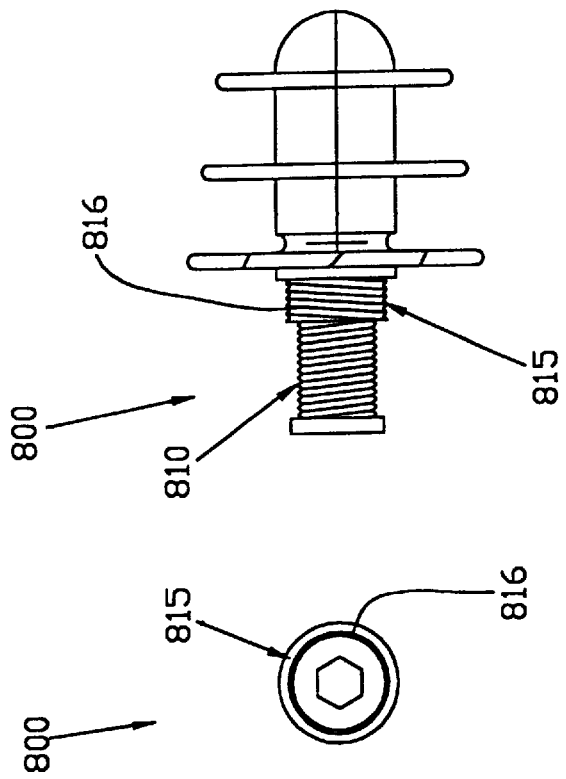
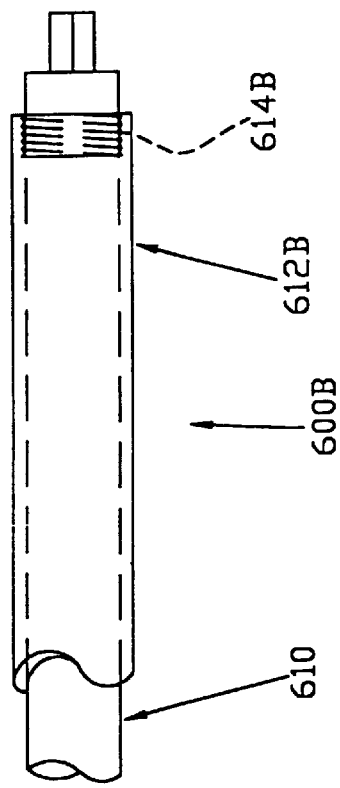
Fig. 56

BONE CEMENT PLUG FOR DEPLOYMENT IN A BONE CANAL

FIELD OF THE INVENTION

This invention relates to surgical apparatus and procedures in general, and more particularly to bone cement plugs of the sort used in conjunction with bone cement dispensers to compact bone cement into bone canals during total joint replacement surgeries.

BACKGROUND OF THE INVENTION

Bone cement plugs are well known in the art. Such devices are generally used in conjunction with bone cement dispensers to compact bone cement into a bone canal before fixing a prosthetic device in that bone canal. By way of example, bone cement plugs are commonly used in conjunction with bone cement dispensers to compact bone cement into the intramedullary canal of the femur before fixing the femoral stem of an artificial hip in that canal.

More particularly, in total joint replacement surgeries such as hip and shoulder replacements, bone cement is commonly used to fix the stems of the prosthetic devices into the intramedullary canals of the joint's bones. In this respect it has generally been found that a prosthetic device will be more securely fixed in a bone canal if the bone cement is well packed into the bone canal before the distal end of the prosthetic device is positioned in the bone canal.

To this end, after initial preparation and cleaning of the bone canal, the distal end of the canal is occluded with a plug. The bone cement plug serves to limit uncontrolled flow of bone cement into the distal portion of the bone canal. Ideally, the bone cement plug limits the column of bone cement to about 1 to 2 cm beyond the distal tip of the stem of the prosthesis. After the plug has been set at the distal end of the bone canal, the bone cement is then injected into the distal-most part of the bone canal, adjacent to the plug, using a bone cement dispenser having a long nozzle. The bone canal is then filled with bone cement in a retrograde fashion, by withdrawing the nozzle of the bone cement dispenser from the distal end of the bone canal to the proximal end of the bone canal as the cement issues from the nozzle. Such retrograde filling helps avoid trapping air in the distal-most part of the bone canal.

After the bone canal has been filled with bone cement, a bone canal pressurizer is then connected to the bone cement dispenser. The pressurizer is pressed against the open end of the bone so as to occlude the bone canal. More cement is then injected into the bone canal through the pressurizer and under pressure. Under such pressurization, the cement in the bone canal intrudes into the interstices of the inner surface of the bone canal. When the bone cement thereafter sets, a micro-interlock is established between the cement and the irregularities of the interior surface of the bone canal. This significantly enhances fixation of the prosthetic device in the bone canal.

Ideally, a bone cement plug should be easy to deploy at the distal end of the bone canal, effective in closing off that bone canal and, in the event that the bone cement plug subsequently needs to be removed, easy to retrieve from the distal end of the bone canal. The bone cement plug must also be bio-compatible with the patient. Furthermore, the bone cement plug should be inexpensive to produce.

A variety of bone cement plugs are known in the art. See, for example, the bone cement plugs described and illustrated in U.S. Pat. Nos. 4,245,359; 4,276,659; 4,293,962; 4,302, 855; 4,344,190; 4,447,915; 4,627,434; 4,686,973; 4,697,584; 4,745,914; 4,936,859; 4,950,295; 4,994,085; 5,061,287; 5,078,746; 5,092,891; 5,376,120; and 5,383,932. See also, for example, the bone cement plug described and illustrated in British Patent Document No. 2,253,564A. See also, for example, the publication entitled "Polyethylene medullary plug according to Stuhmer/Weber" distributed by ALLO PRO AG of Switzerland. See also related apparatus described and illustrated in U.S. Pat. Nos. 4,011,602; 4,523,587; and 4,904,267. See also related apparatus described and illustrated in European Patent Document No. 0,006,408 B1; and PCT Patent Document No. WO 94/15544.

Unfortunately, however, all of the bone cement plugs developed to date tend to suffer from one or more significant disadvantages.

More particularly, in general, the fixation of the bone cement plug depends on the friction between the inner wall of the bone canal and the bone cement plug. Currently, the most common surgical technique is to first measure the size of the prepared bone canal. This involves sequentially inserting a number of "sizers" into the bone canal so as to determine the gross cross-sectional diameter of the canal at the desired depth. Having thus determined the size of the canal, an over-sized plug is inserted into the canal so as to occlude the distal portion of the bone canal. If the bone cement plug is not sufficiently over-sized, or if the design of the plug is overly-deformable, the bone cement plug's engagement with the inner wall of the bone canal will be less than optimal. During the pressurization phase or during insertion of the prosthesis, the increased pressure of the bone cement can then cause the insufficiently-anchored bone cement plug to migrate distally. However, if the bone cement plug is greatly over-sized, and/or if the design of the bone cement plug is overly rigid, the bone cement plug cannot be inserted into the bone canal to the desired depth. Excessively forceful insertion of the bone cement plug can cause the wall of the bone canal to fracture.

Many of the current bone cement plugs cannot adequately anchor against the wall of the bone canal located beyond the isthmus, i.e., against that portion of the bone canal located beyond the narrowest part of the canal. This is because the largest size of the bone cement plug is limited by the need for the bone cement plug to pass through the narrowest part of the canal. In other words, a smaller than desired plug size is chosen.

Various expandable plugs are designed to addressed the above issues. However, such known bone cement plugs suffer from a number of drawbacks such as difficulty in manufacturing, inadequate fixation, the complexity of the insertion tools, etc.

OBJECTS OF THE INVENTION

Accordingly, the primary object of the present invention is to provide an improved bone cement plug for deployment in a bone canal.

Another object of the present invention is to provide a bone cement plug which is easy to deploy at the distal end of the bone canal, effective in closing off that bone canal and, in the event that the bone cement plug subsequently needs to be removed, easy to retrieve from the distal end of the bone canal.

Still another object of the present invention is to provide a bone cement plug which is bio-compatible with the patient, and which is inexpensive to produce.

Yet another object of the present invention is to provide an insertion tool for deploying the bone cement plug at the distal end of the bone canal and, in the event that the bone cement plug subsequently needs to be removed, an extraction tool for retrieving the bone cement plug from the distal end of the bone canal.

And another object of the present invention is to provide an improved method for closing off the distal end of a bone canal.

SUMMARY OF THE INVENTION

These and other objects of the present invention are addressed by the provision and use of a novel bone cement plug and its associated insertion and extraction tools.

The novel bone cement plug comprises a core comprising a substantially cylindrically-shaped base portion defining a threaded bore therein extending axially and distally from a proximal end of the base portion; a first leg portion depending from and extending distally from the base portion; and a second leg portion depending from and extending distally from the base portion and opposed to the first leg portion; the base portion threaded bore being adapted to receive an expander screw to wedge apart the first and second leg portions, whereby to expand the core widthwise to secure the plug in the bone canal; and the expander screw, the screw comprising a generally cylindrically-shaped body having a tapered distal end, and a proximal end in which is disposed a threaded bore, external threads disposed on the body, and an annular flange extending outwardly from the proximal end of the body, the screw being threadedly engageable with the core threaded bore for advancement of the screw into the plug for said wedging apart of the first and second legs.

Preferably, the novel bone cement plug is constructed so that the screw threaded bore is provided with first and second sets of threads, the first set of threads being adapted to receive a screw insertion tool, and said second set of threads being adapted to receive a screw extraction tool.

The novel insertion tool comprises a rod having at a distal end thereof a tip portion of reduced diameter, the tip portion including a distal-most cylindrically-shaped portion adapted to be non-threadedly received by the screw second set of threads, and a proximal-most threaded portion adapted to be threadedly received by the screw first set of threads, whereby the insertion tool is adapted to advance the screw into the plug.

The novel extraction tool comprises a rod having at a distal end thereof a tip portion of reduced diameter, the tip portion including a distal-most threaded portion adapted to be threadedly received by the screw second set of threads, and a proximal-most cylindrically-shaped portion adapted to be non-threadedly received by the screw first set of threads, whereby the extraction tool is adapted to withdraw the screw from the plug.

The foregoing apparatus is intended to be used as follows, but does not exclude other methods of use obvious to those skilled in the art. In one method of use, three cores (small, medium and large) are sterilely packaged with the insertion tool and central screw, with the central screw loaded onto the medium sized core. Each core size covers a range of different bone canal sizes. The three cores will cover the whole range of bone canal sizes expected to be encountered by the surgeon. The medium sized core will be adequate for the majority of the bone canals. Also included in the sterile package is a canal sizer consisting of a smaller (e.g., 12 mm) ball on one end of a rod and a larger (e.g., 16 mm) ball on the other end of the rod. One of the balls can be unscrewed from the rod, exposing a tip designed to fit the central screw as an extraction tool.

After preparing the bone canal in the standard fashion, the canal can be sized with the canal sizer to determine to what size range the bone canal belongs. Most surgeons who are familiar with joint replacements have a rough idea as to the size of the canal. If the canal is in the range of the smaller size, the surgeon will attempt to insert the smaller ball into the canal to the desired depth. If the surgeon is unable to insert the smaller ball to the desired depth, then the surgeon will have to use the small sized core. It goes without saying that if the smaller ball can be inserted to the desired depth, then the medium sized core should be adequate. Similarly, for a larger canal, if the larger ball can be inserted to the desired depth, then a large sized core must be used. At any rate, with the initial rough idea as to the size range of the canal, the surgeon will only have to size the canal once to determine the size of the core which is to be used.

After selecting the proper core, the plug is inserted into the bone canal to the desired depth, and then the handle of the insertion tool is rotated to advance the central screw. This will cause the core of the plug to expand and thus increase the fixation of the plug against the inner wall of the bone canal.

If one should make an error in the choice of the size of the plug (either too loose or unable to be inserted to the desired depth), the plug can be extracted from the canal in the following fashion. If the plug is not tightly fixated against the inner wall of the bone canal, the plug can be pulled out of the canal by withdrawing the insertion tool. If the core of the plug is expanded and tightly jammed against the wall of the canal, then the extraction tool can be used to back out the central screw to allow the core of the plug to collapse. This is done by unscrewing one of the balls on the sizer tool. This exposes the extractor tip. The extractor tip is inserted into the central screw and rotated counter-clockwise to engage the central screw. When the central screw is fully engaged, the surgeon continues to rotate the extractor tip counter-clockwise to partially back out the central screw. This allows the core to collapse and the plug can then be easily extracted from the canal.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 2 is a side elevational view of a bone cement plug formed in accordance with the present invention;

FIG. 3 is a sectional view of the bone cement plug shown in FIG. 2;

FIG. 4 is a sectional view taken along line 4—4 of FIG. 3;

FIG. 5 is a side elevational view of the bone cement plug shown in FIG. 2, except with the plug shown in its expanded position;

FIG. 6 is a sectional view of the bone cement plug shown in FIG. 5;

FIG. 7 is a sectional view taken along line 7—7 of FIG. 6;

FIG. 8 is a top plan view of the bone cement plug shown in FIG. 2;

FIG. 9 is a side view, partially in section, showing the bone cement plug of FIG. 2 inserted in a bone canal;

FIG. 10 is a side view, partially in section, showing the bone cement plug of FIG. 5 deployed in a bone canal;

FIG. 11 is a sectional view of the bone cement plug's expander screw;

FIG. 12 is a side elevational view of the distal end of an insertion tool formed in accordance with the present invention;

FIG. 13 is a side view of the distal end of an extraction tool formed in accordance with the present invention;

FIGS. 24–27 are schematic side views, partially in section, showing another method of deploying the bone cement plug within the bone canal;

FIG. 41 shows the proximal end of an alternative form of insertion tool;

FIG. 42 shows the bone canal plug of FIGS. 35–40 mating with a corresponding insertion tool;

FIG. 49 shows the bone canal plug of FIGS. 43–48 mating with a corresponding insertion tool;

FIG. 56 shows the bone canal plug of FIGS. 50–55 mating with a corresponding insertion tool.

DETAILED DESCRIPTION OF THE PREFERRED EMBODIMENT

Figure 1:
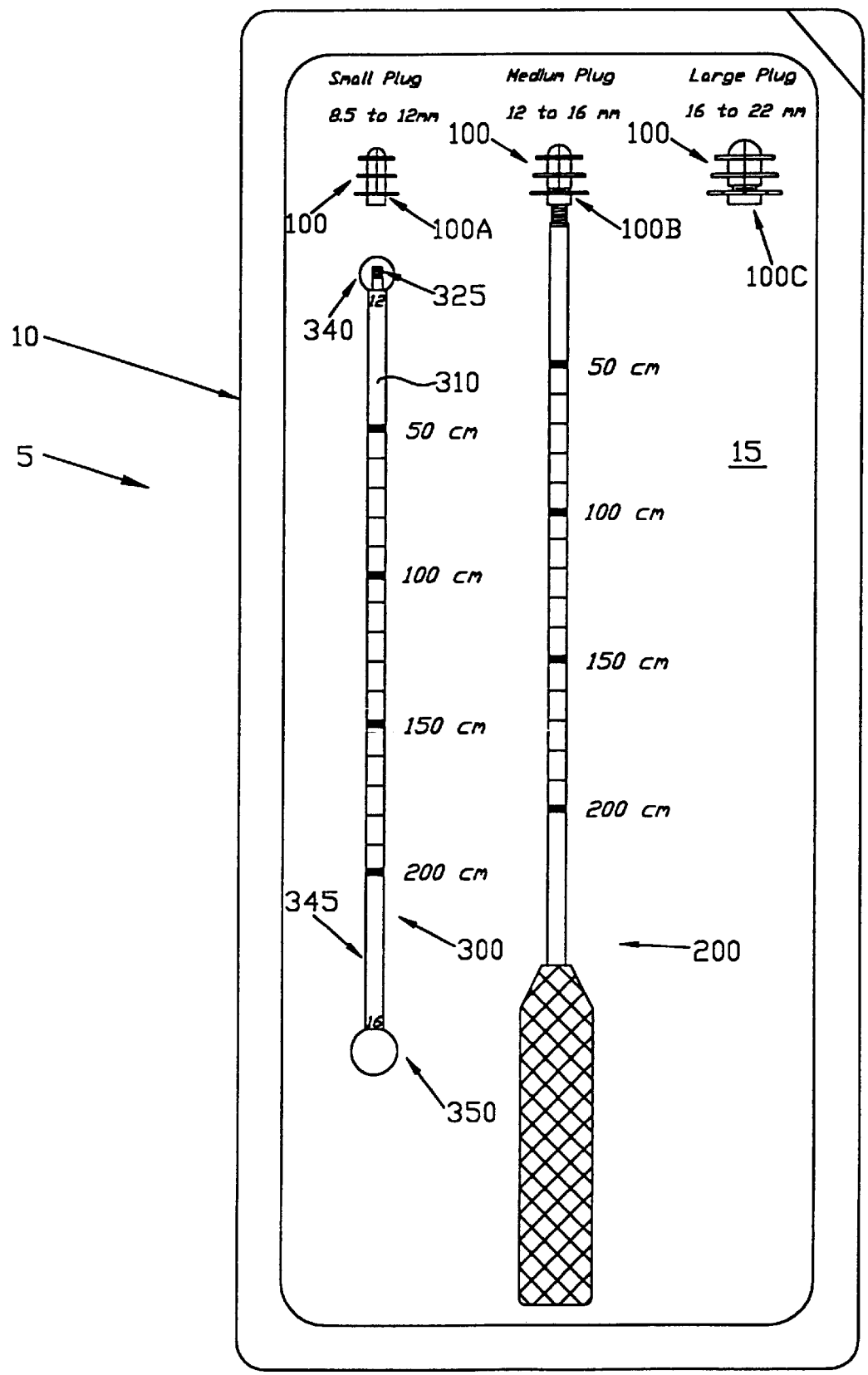
FIG. 1 is a top plan view of a bone cement plug kit formed in accordance with the present invention.

Looking first at FIG. 1, there is shown a bone cement plug kit 5 which comprises a preferred embodiment of the present invention.

Bone cement plug kit 5 generally comprises a tray 10 holding a plurality of bone cement plugs 100, an insertion tool 200 and an extraction tool 300. Preferably, tray 10 is filled with its constituent components 100, 200 and 300 at the time of manufacture, and then the tray is sealed with a transparent top tear sheet 15 so as to form a pre-packaged kit which may thereafter be opened at the time of use. As is well known in the art, tray 10 and its constituent components 100, 200 and 300 may be sterilized either before or after the package is sealed with top tear sheet 15.

Bone cement plugs 100 are shown in greater detail in FIGS. 2–7. Each bone cement plug 100 generally comprises a core 105 and an expander screw 110.

Each core 105 generally comprises a substantially cylindrically-shaped base portion 115 defining a threaded bore 120 (FIGS. 3 and 6) therein. Threaded bore 120 extends axially and distally from a proximal end surface 125 of base portion 115. A first leg portion 130 depends from, and extends distally from, base portion 115. A second leg portion 135 also depends from, and extends distally from, base portion 115. First and second leg portions 130, 135 normally sit in opposed relation to one another (FIGS. 2–4).

The base portion's threaded bore 120 is adapted to receive expander screw 110 so as to wedge apart the first and second leg portions 130, 135 (FIGS. 5–7), whereby to expand core 105 widthwise so as to transform the cross-sectional profile of the distal portion of bone cement plug 100 from circular (FIG. 4) to elliptical (FIG. 7). Such a transformation can be used to secure the bone cement plug in a bone canal, as will hereinafter be discussed in further detail.

To this end, expander screw 110 in turn comprises a generally cylindrically-shaped body 140 (FIGS. 3 and 6) having a tapered distal end 145 and a proximal end 150. A threaded blind hole 155 extends distally into the expander screw's body from its proximal end surface 159. External threads 160 are disposed on body 140, and an annular flange 165 extends outwardly from the proximal end of body 140. The expander screw's external threads 160 are threadedly engageable with the core's threaded bore 120, whereby clockwise rotation of expander screw 110 relative to core 105 will cause the expander screw to advance into the core so as to wedge apart the core's first and second leg portions 130, 135 (FIGS. 5–7).

More particularly, bone cement plug 100 is arranged so that first and second leg portions 130, 135 normally (i.e., prior to expansion) abut one another (FIGS. 2–4) and together form a substantially cylindrical configuration of substantially the same diameter as the diameter of base portion 115 (FIGS. 2 and 3). However, bone cement plug 100 is also arranged so that, after expansion, first and second leg portions 130, 135 are separated from each other in diametrically opposed outwardly directions (FIGS. 5–7), whereby to assume a generally oval configuration in the bone canal. It will be appreciated that first and second legs portions 130, 135 cooperatively define a tapered bore portion 167 (FIG. 3) which is a co-axial extension of the core's threaded bore 120. Tapered bore portion 167 is formed so as to have a geometry which is complementary to the geometry of the expander screw's tapered distal end 145 (FIG. 3), whereby distal progress of the expander screw's tapered distal end 145 along the core's tapered bore portion 167 will wedge apart the core's first and second leg portions 130, 135.

In the preferred embodiment of the invention, each bone cement plug 100 also comprises a plurality of annular flanges 170 (FIGS. 2–7) extending radially outwardly from core 105. Flanges 170 are adapted so as to be flexibly engageable with the wall of a bone canal, as will hereinafter be discussed in further detail. Preferably three flanges 170A, 170B, and 170C are provided. In one form of the invention, flanges 170 have an increasing diameter as they approach the core's proximal end surface 125 and a decreasing diameter as they approach the core's distal end, such that flange 170A has a diameter greater than flange 170B, and flange 170B has a diameter greater than flange 170C, as shown in FIGS. 2 and 3.

In the preferred form of the invention, at least the proximal-most flange 170A is provided with a plurality of slits 185 (FIGS. 2, 5 and 8) which extend radially inwardly from the outer perimeter of the flange. Slits 185 extend inwardly toward an inner edge 190 (FIGS. 3, 6 and 8) where flange 170A and base portion 115 meet, but slits 185 terminate at a point spaced from the inner edge of the flange. Preferably, each of the slits 185 extends through flange 170A at an angle to the lengthwise axis 187 of bone cement plug 100, as illustrated in FIGS. 2 and 5. Typically, slits 185 extend at an angle of about 30°–60° to the lengthwise axis of bone cement plug 100. In one particular form of the invention, slits 185 extend at an angle of approximately 45° to the lengthwise axis of the bone cement plug.

In the preferred embodiment of the invention, the proximal-most flange 170A preferably has a diameter which exceeds the diameter of the bone canal, such that the proximal-most flange 170A will be compressed somewhat by the wall of the bone canal during deployment, as will hereinafter be discussed in further detail. In such a situation, slits 185 permit peripheral portions of the proximal-most flange 170A to override other adjacent peripheral portions of the proximal-most flange, whereby the flange can effectively size itself to the interior dimensions of the bone canal (FIGS. 9 and 10).

As noted above, slits 185 are formed in at least the proximal-most flange 170A. However, it should also be appreciated that slits 185 may be formed in one or more of the other flanges (i.e., flange 170B and/or flange 170C) if desired.

In one preferred form of the invention, the proximal-most flange 170A extends outwardly from base portion 115, and the distal-most flange 170C includes a first portion 170C' (FIGS. 2, 3, 5 and 6) which extends outwardly from first leg portion 130, and a second portion 170C" (FIGS. 2, 3, 5 and 6) which extends outwardly from second leg portion 135. Preferably intermediate flange 170B includes a first portion 170B' which extends outwardly from first leg portion 130, and a second portion 170B" which extends outwardly from second leg portion 135.

Referring next to FIGS. 2 and 5, it will be seen that the core's base portion 115 and two leg portions 130, 135 define therebetween an annular groove 195. Preferably annular groove 195 is disposed just distal to flange 170A. A pair of diametrically opposed, horizontally-extending slits 196 (only one of which is shown in the drawings) are positioned in annular groove 195. Slits 196 extend widthwise through the side wall of the plug and, more particularly, through proximal and substantially equal portions of the first and second legs 130, 135. Groove 195 and slits 196 together serve to facilitate outward bending of legs 130, 135 upon advancement of expander screw 110 into core 105 (FIGS. 5 and 10).

Referring next to FIG. 11, it will be seen that the expander screw's threaded bore 155 is provided with first and second sets of threads 156, 157. The second set of threads 157 is in axial alignment with the first set of threads 156; is of smaller inside diameter than the first set of threads 156; and is disposed distally of the first set of threads 156. The first set of threads 156 is adapted to receive insertion tool 200, as will be discussed in further detail below, and the second set of threads 157 is adapted to receive extraction tool 300, as will also be discussed in further detail below. It should be appreciated that(i) the first set of threads 156 is oriented in the same direction as the threads in the core's threaded bore 120, and (ii) first and second sets of threads 156, 157 have a reverse pitch from one another, as will also be discussed in further detail below.

Bone cement plugs 100 are formed out of a material which is bio-compatible. Preferably, bone cement plugs 100 are formed out of a material selected from a group of materials consisting of metal, plastic, bio-absorbable materials, and metal-plastic composites. By way of example, bone cement plugs 100 might be formed out of a plastic material, e.g., polyethylene or polypropylene. Alternatively, core 105 might be made out of plastic material and expander screw 110 might be made out of a metal. In one preferred embodiment of the invention, bone cement plug 100 is formed so that its flanges 170 are somewhat flexible, whereby they may more easily conform to the cross-sectional profile of the bone canal.

A distal portion 205 of insertion tool 200 is shown in FIG. 12. Insertion tool 200 comprises a rod 210 having, at a distal end 215 thereof, a tip portion 220 of reduced diameter. Tip portion 220 includes a distal-most cylindrically-shaped portion 225 adapted to be non-threadedly received by the expander screw's second set of threads 157, and a proximal-most threaded portion 230 adapted to be threadedly received by the expander screw's first set of threads 156, such that insertion tool 200 can, by rotation thereof, mate with expander screw 110 and thereafter advance screw 110 into core 105. Rod 210 is provided, at the juncture with rod tip portion 220, with an annular shoulder 235 for engagement with the expander screw's annular flange 165.

Annular shoulder 235 can be formed with a planar surface for mating with a corresponding planar surface atop the expander screw's annular flange 165. Alternatively, annular shoulder 235 may be provided with ratchet teeth 240 (FIG. 12), and expander screw 110 may be provided with complementary ratchet teeth 169 (FIG. 11), such that engagement of the rod's ratchet teeth 240 and the expander screw's counterpart ratchet teeth 169 ensures that rod 210 will begin turning expander screw 110 as the rod's annular shoulder 235 approaches the expander screw's annular flange 165. Such a construction helps prevent binding between insertion tool 200 and expander screw 110 due to any overtightening of the insertion tool relative to the expander screw. This situation can be of particular concern where the expander screw is formed out of a material which is significantly softer than the material out of which the rod is formed, e.g., where the rod is formed out of metal and the expander screw is formed out of plastic.

A distal portion 305 of extraction tool 300 is shown in FIG. 13. Extraction tool 300 comprises a rod 310 having, at a distal end 315 thereof, a tip portion 320 of reduced diameter. Tip portion 320 includes a distal-most threaded portion 325 adapted to be threadedly received by the expander screw's second set of threads 157, and a proximal-most cylindrically shaped portion 330 adapted to be non-threadedly received by the expander screw's first set of threads 156, such that extraction tool 300 can, by rotation thereof, withdraw screw 110 from core 105. Rod 310 is provided, at the juncture with rod tip portion 320, with an annular shoulder 335 for engagement with screw flange 165 (or with the screw's ratchet teeth 169, if the same should be provided on screw 110).

It should be appreciated that the insertion tool's threaded portion 230 and the retractor tool's threaded portion 325 have a reverse pitch from one another, as will be discussed in further detail below. The expander screw's first set of threads 156 are engaged by the insertion tool's threaded portion 230 by turning insertion tool 200 into screw 110 in a first rotative direction (e.g., clockwise), whereupon further rotation of insertion tool 200 in that same direction will advance screw 110 into core 105 so as to expand the core. Correspondingly, the expander screw's second set of threads 157 are engaged by the extraction tool's threaded portion 325 by turning extraction tool 300 into screw 110 in an opposite direction (e.g., counter-clockwise), whereupon further rotation of extraction tool 300 in that same opposite direction will withdraw screw 110 from core 105 so as to permit the core to return to its original, non-expanded configuration.

Returning now to FIG. 1, it will be seen that extraction tool 300 may also be used as a sizing tool by removably mounting a sizing ball 340 on threaded portion 325. If desired, the proximal end 345 of a extraction tool's rod 310 may have a second sizing ball 350 mounted thereon. By advancing a sizing ball of known diameter into the bone canal, the user may obtain an indication as to the internal diameter of the canal and, therefrom, select an appropriate size of bone cement plug for disposition within that bone canal.

By way of example, but not limitation, in the case where bone cement is to be used in a total hip replacement procedure and, more specifically, in the case where bone cement is to be injected into the intramedullary canal of the femur of an adult, the following method of use has been found to be appropriate.

Figure 14:
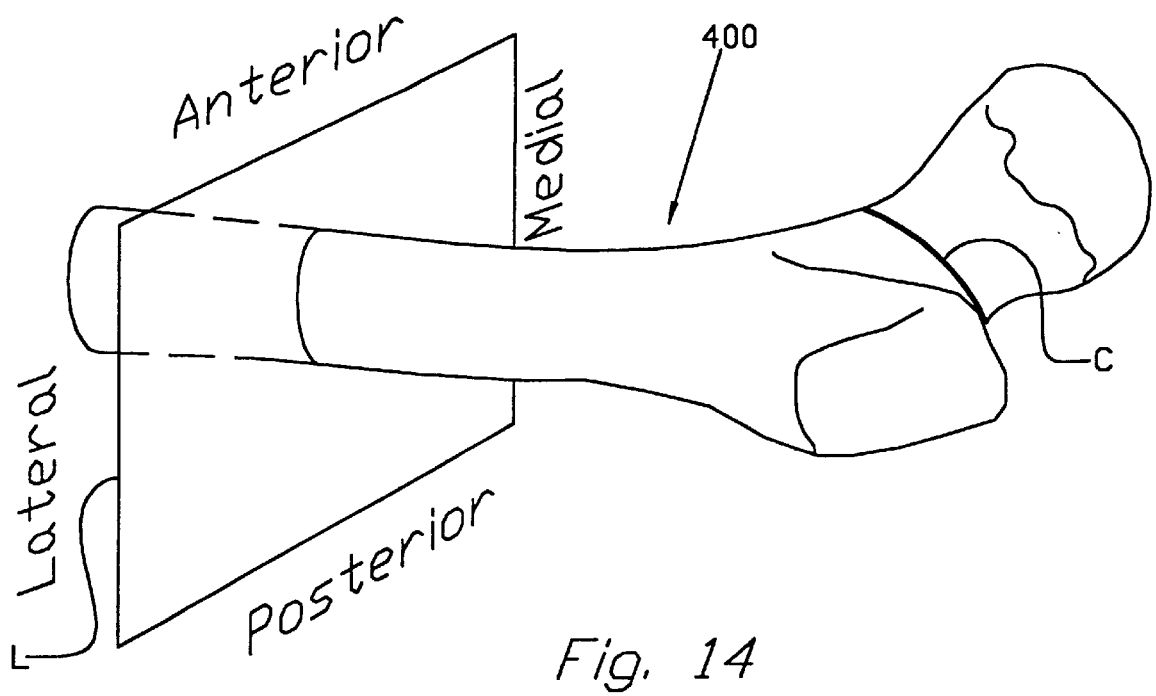
FIG. 14 is a schematic perspective view of a human femur bone.
Figure 15:
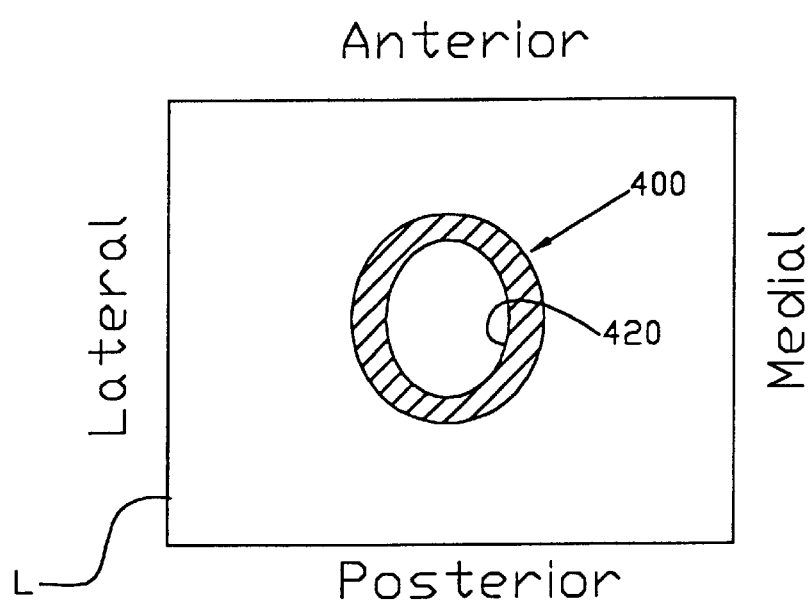
FIG. 15 is a sectional view taken through the plane L of FIG. 14.

A transverse cut C is first made through the patient's femur 400 (FIG. 14), exposing the intramedullary canal 420 (FIG. 15) which is generally oval-shaped in cross-section at the location L where bone cement plug 100 will be positioned. Canal 420 is cleaned out and made ready for receipt of the bone cement and the prosthetic femoral stem (not shown) in ways well known in the art.

A bone cement plug 100 is selected by size for insertion into bone canal 420. The sizing balls 340, 350 may be used for guidance as to the approximate size plug required. Measurement markings may be placed along rod 310 of extraction tool 300 (FIG. 1) so as to help the user determine the depth of the sizing balls as they are inserted into the bone canal. A plug of the type shown in FIGS. 2 and 3 is then assembled, if not previously assembled, so as to join expander screw 110 and core 105. Preferably, however, a bone cement plug 100 is provided already assembled, as shown in the bone cement plug kit 5 depicted in FIG. 1. Preferably, bone cement kit 5 is arranged to form a plurality of bone cement plugs 100 of differing sizes, e.g., plugs 100A, 100B and 100C (FIG. 1). By way of example, bone cement plug 100A might be sized to accommodate bone canals having a diameter (along the long axis) of between 8.5 mm and 12 mm, bone cement plug 100B might be sized so as to accommodate bone canals having a diameter (along the long axis) of between 12 mm and 16 mm, and bone cement plug 100C might be sized so as to accommodate bone canals having a diameter (along the long axis) of between 16 mm and 22 mm. If desired, bone cement kit 5 may comprise one bone cement plug already assembled (e.g., bone cement plug 100B in FIG. 1), and two additional bone cement plugs (e.g., bone cement plugs 100A and 100C in FIG. 1) which are assembled, in the event they are needed, by combining their respective cores with the expander screw 110 from bone cement plug 100B.

Figure 17:
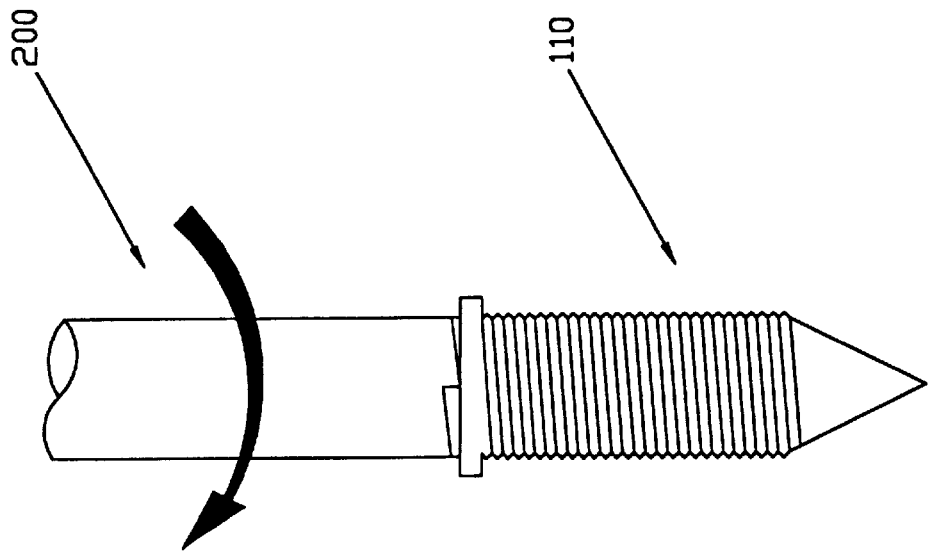
FIGS. 16 and 17 are side elevational views showing the distal end of the insertion tool engaging the bone cement plug's expander screw.
Figure 16:
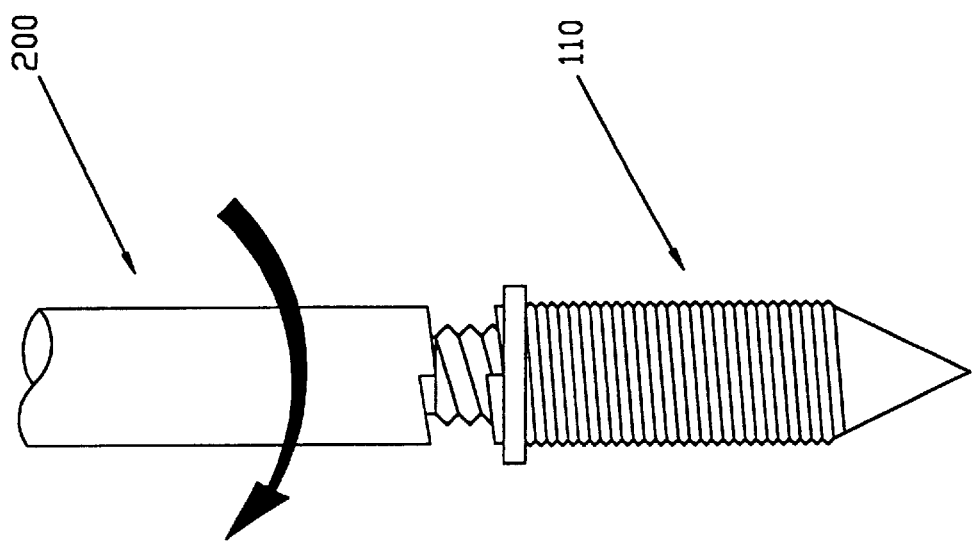

Insertion tool 200 is then screwed into the expander screw's threaded bore 155, the threaded portion 230 (FIG. 12) of insertion tool 200 threadedly engaging the first set of threads 156 (FIG. 11) of screw bore 155. The insertion tool's rod 210 is turned (FIG. 16) so as to advance the rod into screw 110 until the insertion tool's shoulder 235 (FIG. 12) engages the expander screw's flange 165 (FIG. 11) or, if ratchet teeth are provided, until the insertion tool's ratchet teeth 240 (FIG. 12) engage the screw's ratchet teeth 169 (FIG. 11), in the manner shown in FIG. 17.

Figure 18:
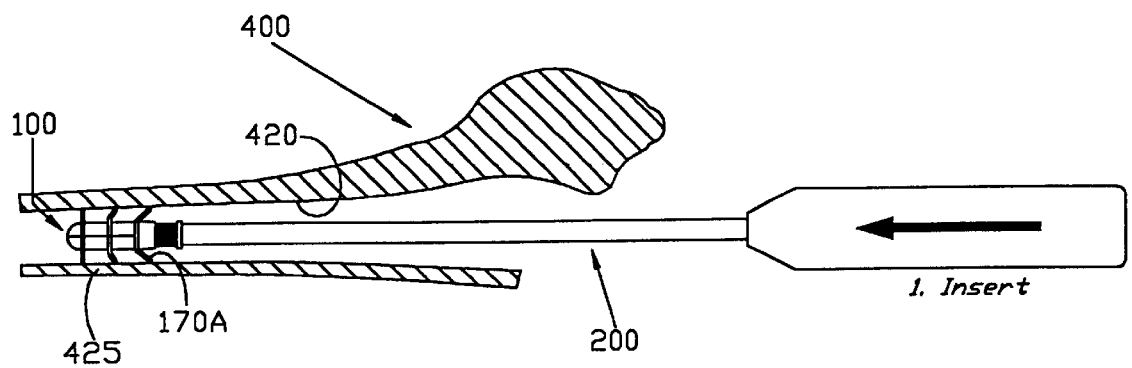
FIGS. 18–20 are schematic side views, partially in section, showing one method of deploying the bone cement plug within a bone canal.

Using insertion tool 200, bone cement plug 100 then is forced into bone canal 420 of femur 400 and moved axially into a selected position within canal 420 (FIG. 18). Measurement markings may be placed along the shaft of insertion tool 200 (FIG. 1) so as to help the user properly locate the bone cement plug at the proper depth along the bone canal. Flange 170A, being compressed by a canal wall 425, is deformed. If flange 170A is provided with slits 185, as shown in FIG. 8, flange 170A generally assumes the configuration depicted in FIG. 9, wherein portions of flange 170A have overridden other portions thereof.

Figure 19:
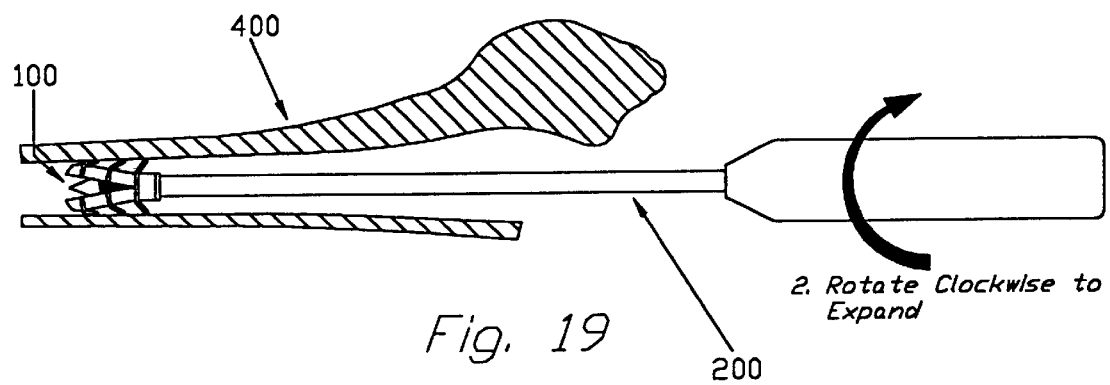
Figure 20:
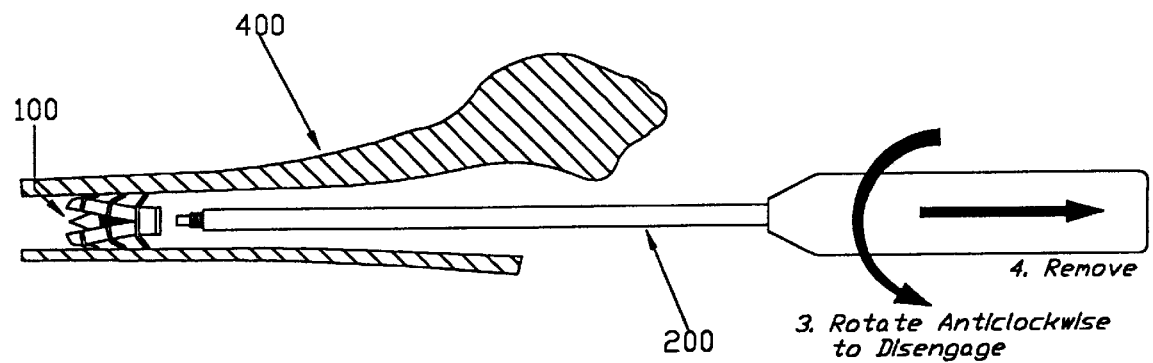

By proper rotation of insertion tool 200 (e.g., clockwise), expander screw 110 is then advanced in core 105 so as to cause expansion of core 105, such that all of the flanges 170 thereof are engaged with, and deformed against, canal wall 425, as shown in FIG. 19. This will generally secure the bone cement plug within bone canal 420. Insertion tool 200 is then rotated in the opposite direction (e.g., counter-clockwise) so as to disengage the insertion tool from expander screw 110 and hence cement plug 100 (FIG. 20). Insertion tool 200 may then be removed from bone canal 420, leaving bone cement plug 100 in place in its expanded condition.

Figure 21:
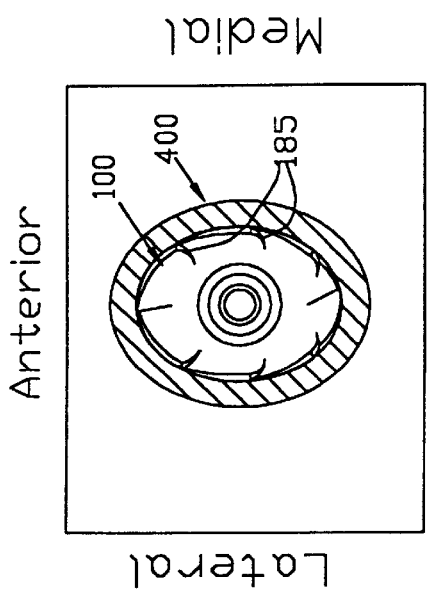
FIGS. 21 and 22 show the bone cement plug disposed in the bone canal, before the plug has been expanded by distal movement of its expander screw, with FIG. 21 looking from proximal to distal, and with FIG. 22 looking from distal to proximal, and with FIG. 22 being a sectional view taken similar to the sectional view of FIG. 4.
Figure 22:
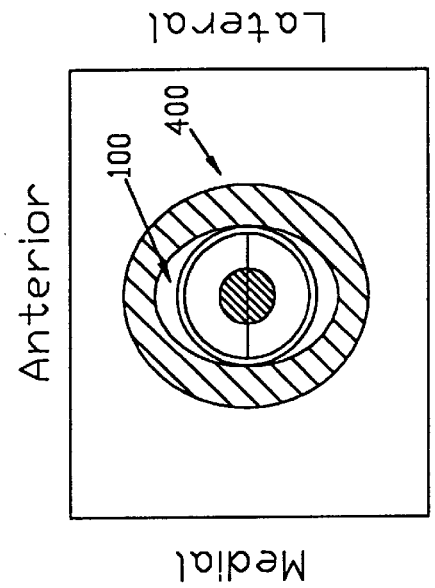
Figure 23A:
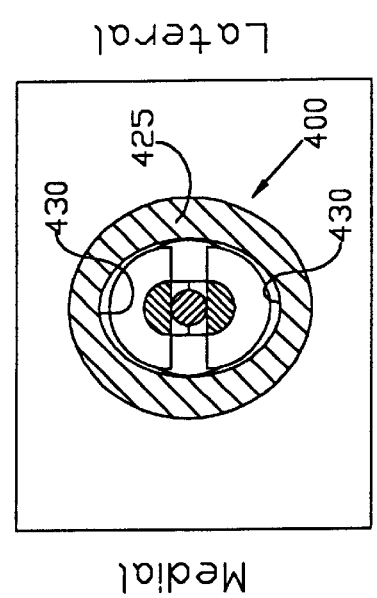
FIG. 23A shows the bone cement plug disposed in the bone canal, after the plug has been expanded by distal movement of its expander screw.
Figure 23B:
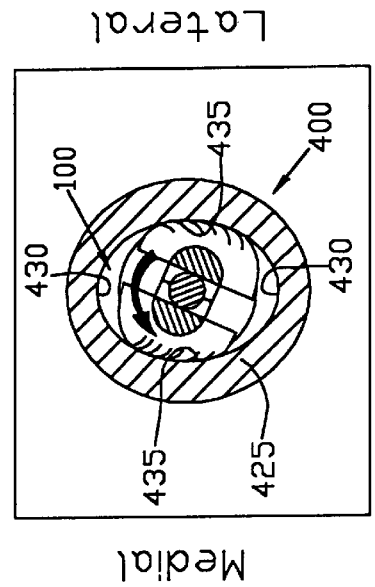
FIG. 23B shows the bone cement plug of FIG. 23A, after the entire bone cement plug has been rotated within the bone canal.

In FIGS. 21 and 22, there is illustrated the configuration of bone cement plug 100 in femur 400, prior to expansion. In FIG. 23A, it will be seen that as bone cement plug 100 expands, it becomes generally oval-shaped so as to substantially conform to the oval cross-section of femur 400. The flanges 170 move oppositely to engage opposite portions 430 of canal wall 425, which are the farthest spaced-apart wall portions. If, for some reason, after expansion, there is not an adequate jamming of bone cement plug 100 in canal 420, the expanded plug 100 may be turned within canal 420, by use of insertion tool 200, such that the extreme outward portions of flanges 170 are squeezed between opposite portions 435 of canal wall 425, which are closest together, so as to deform flanges 170 against wall portions 435, as shown in FIG. 23B.

In the event that the bone cement plug 100 is introduced into bone canal 420 and is determined to only lightly engage canal wall 425 (FIG. 24), tool 200 may be withdrawn from canal 420, along with plug 100. Depending upon the degree of looseness experienced by plug 100 in canal 420, the plug may be replaced by a larger plug or, if the looseness is slight, the plug 100 may be slightly expanded (FIG. 25), re-introduced into canal 420 (FIG. 26), and then further expanded (FIG. 27). Again, if desired, the entire expanded plug 100 may then be rotated within bone canal 420 so as to compress the long axis of the expanded plug 100 against the short axis of the bone canal (FIG. 23B).

Once bone cement plug 100 is lodged in bone canal 420, bone cement may be introduced into the canal under sufficient pressure, in ways well known in the art, to cause the cement to enter the interstices of the canal wall 425.

Figure 28:
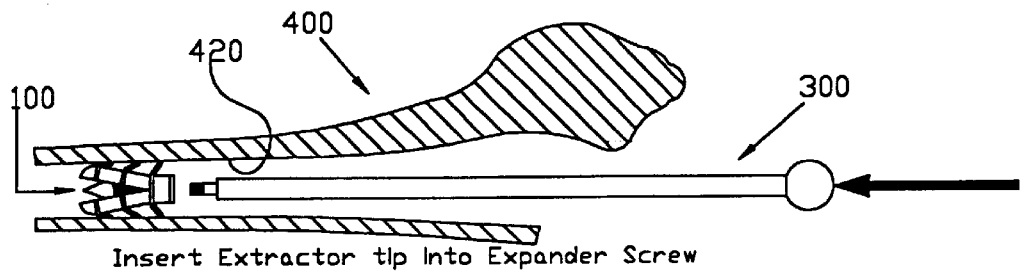
FIGS. 28–32 are schematic side views, partially in section, showing a method for retrieving the bone cement plug from the bone canal.
Figure 29:
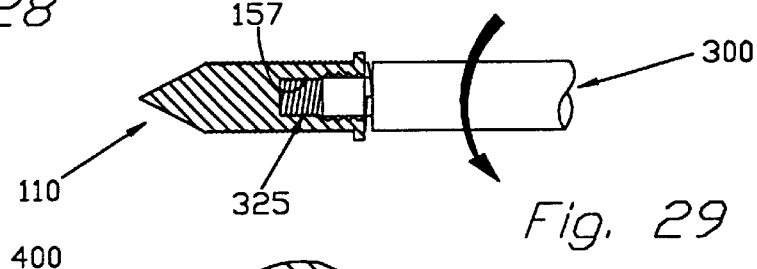
Figure 30:
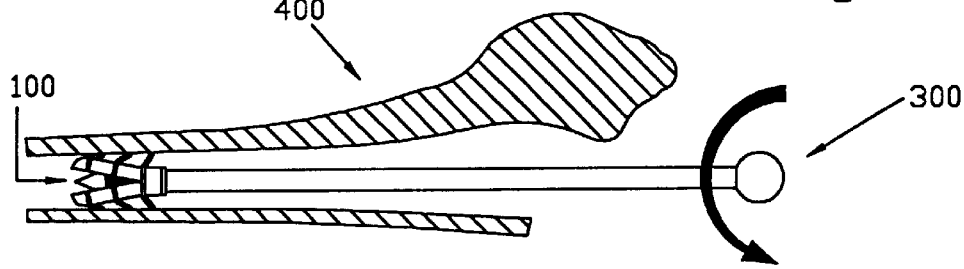
Figure 31:
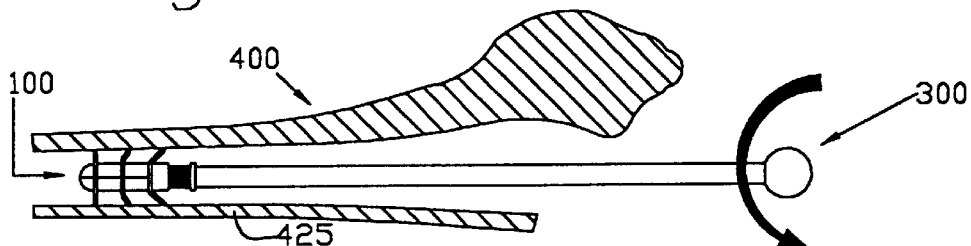
Figure 32:
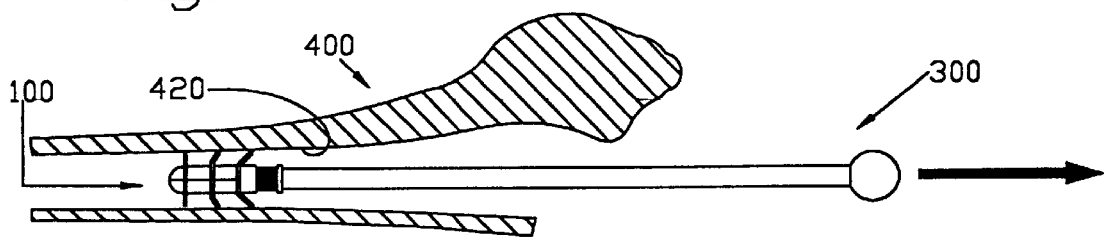

In some circumstances it may be necessary to remove a bone cement plug 100 after it has been deployed in bone canal 420. For example, it may be determined that the bone cement plug is insufficiently engaging the walls of the bone canal, or that the bone cement plug is too big for the bone canal, or that the plug is in the wrong position within the bone canal. To extract bone cement plug 100 from bone canal 420, extraction tool 300 is extended into canal 420 (FIG. 28) and engaged with screw 110, the extraction tool's threaded portion 325 engaging the expander screw's second set of threads 157 (FIG. 29) with counter-clockwise rotation so as to achieve the position shown in FIG. 30. Continued counter-clockwise rotation of extraction tool 300 partially backs out expander screw 110, permitting the core's legs 130, 135 to move toward one another in response to pressure exerted thereon by canal wall 425 (FIG. 31). Thereafter, tool 300 is withdrawn from the site, carrying plug 100 toward the proximal end of canal 420 (FIG. 32) and then out of the canal.

Figure 33:
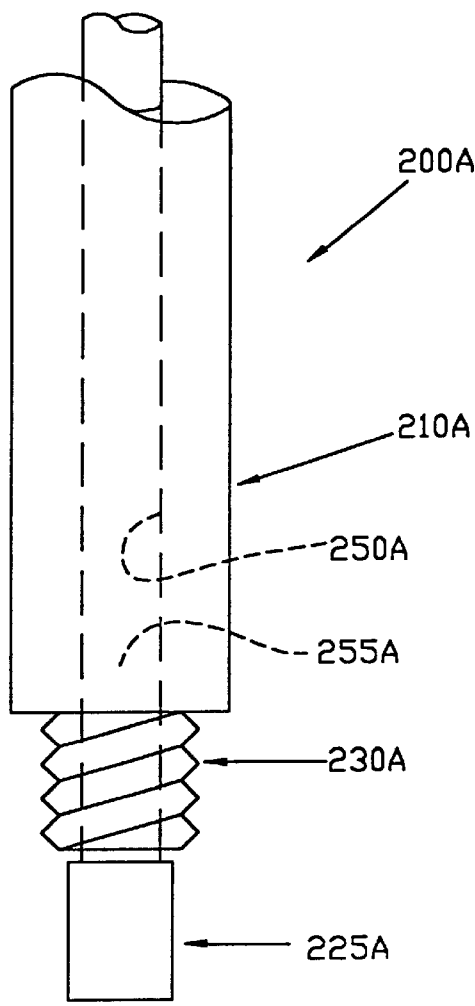
FIGS. 33 and 34 show an alternative form of insertion tool.
Figure 34:
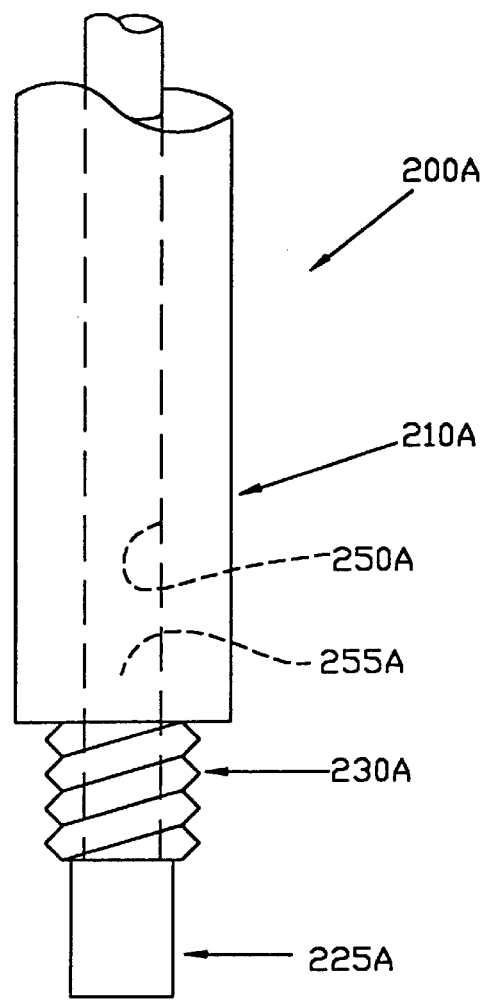
Figure 35:
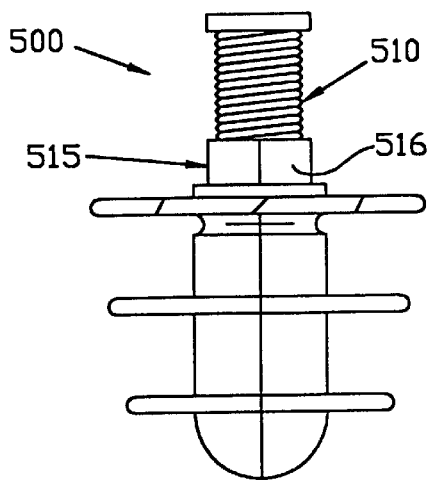
FIGS. 35–40 show an alternative form of bone canal plug.
Figure 38:
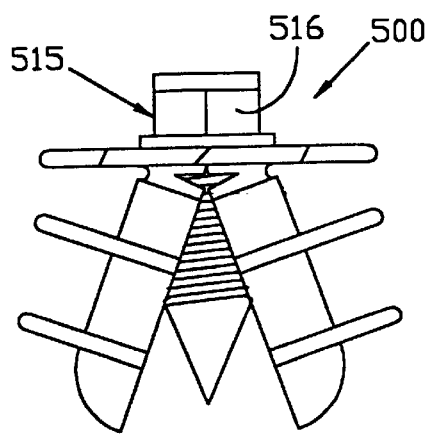
Figure 36:
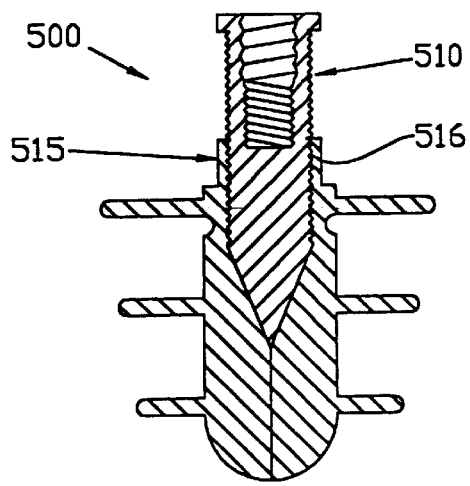
Figure 39:
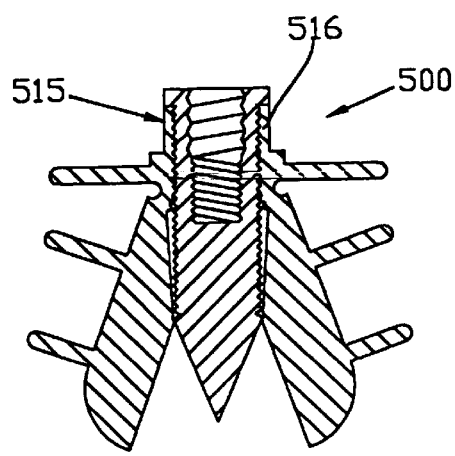
Figure 37:
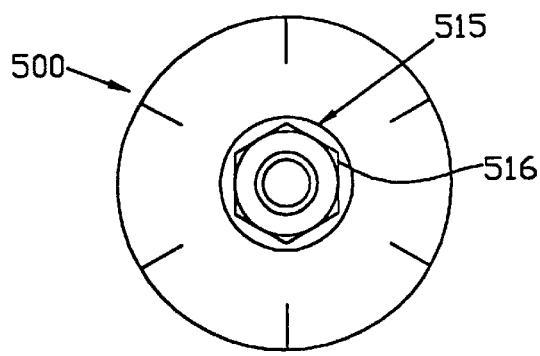
Figure 40:
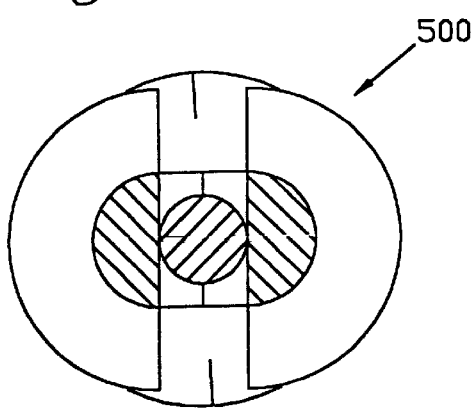
Figure 43:
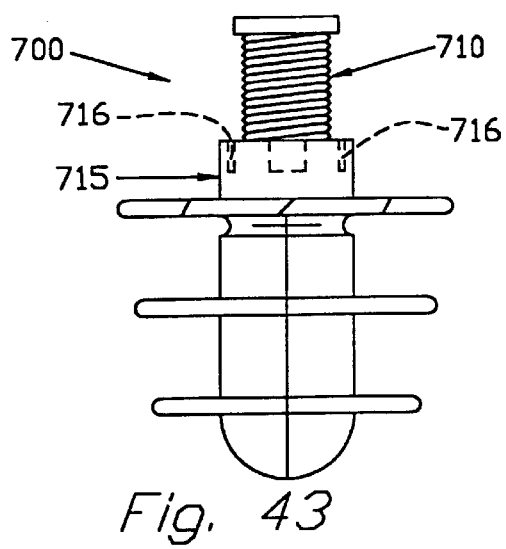
FIGS. 43–48 show another alternative form of bone canal plug.
Figure 46:
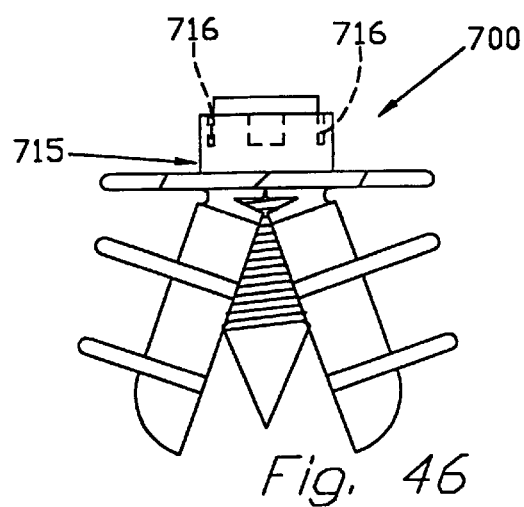
Figure 44:
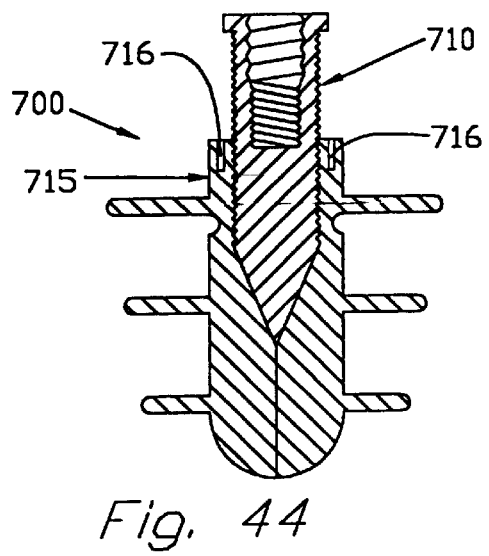
Figure 47:
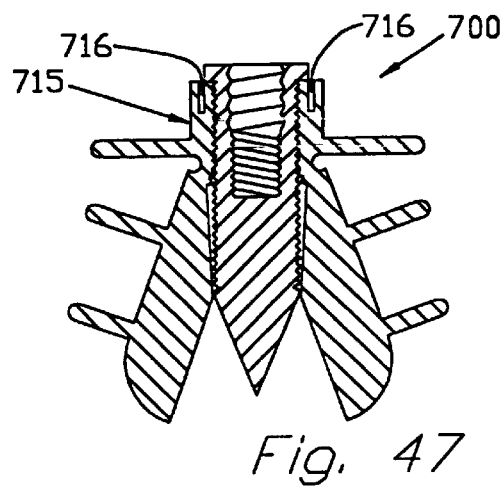
Figure 45:
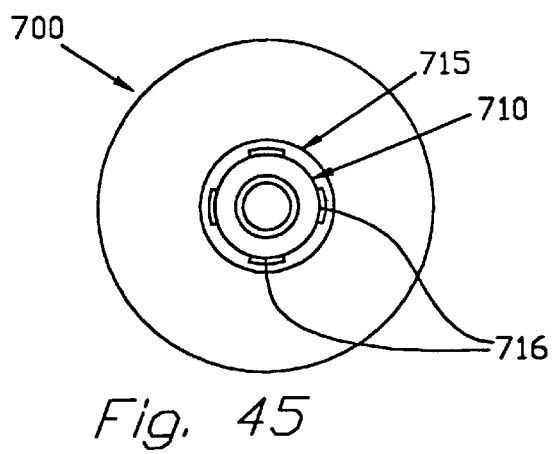
Figure 48:
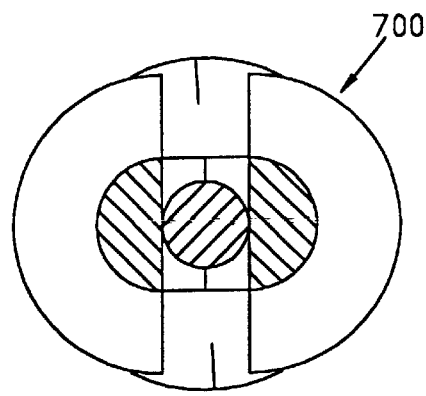
Figure 50:
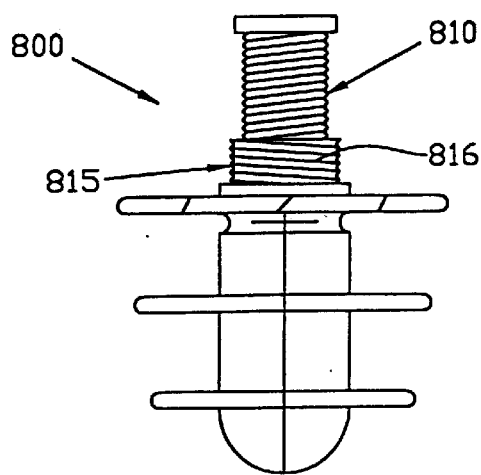
FIGS. 50–55 show still another alternative form of bone canal plug.
Figure 53:
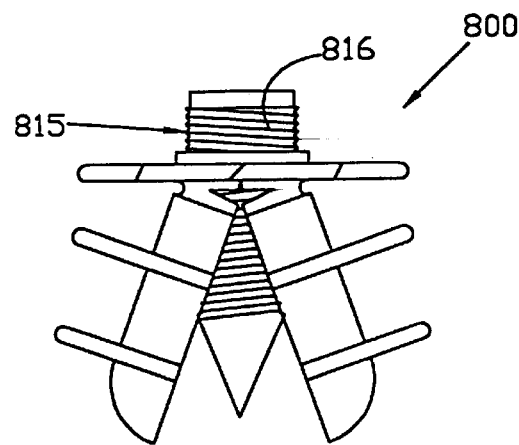
Figure 51:
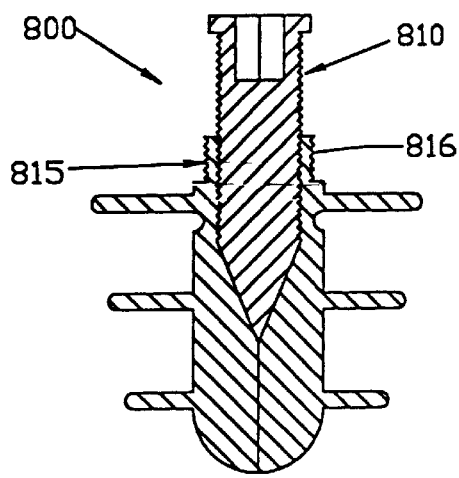
Figure 54:
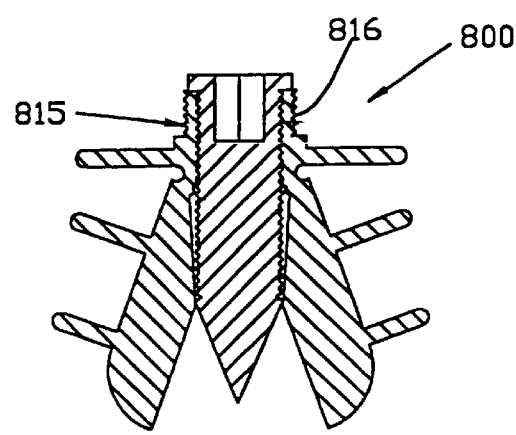
Figure 52:
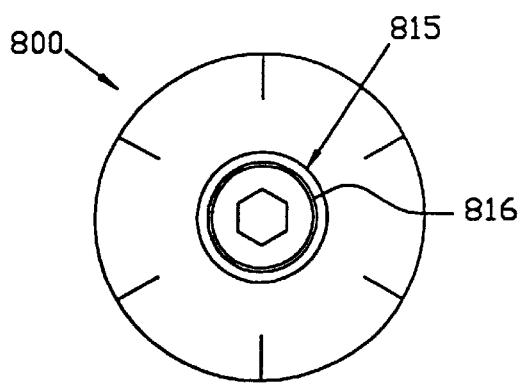
Figure 55:
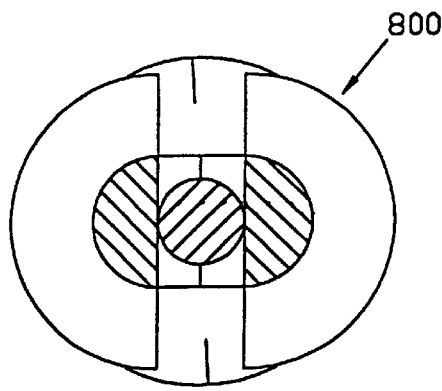

Looking next at FIGS. 33 and 34, there is shown an alternative form of insertion tool 200A. Insertion tool 200A is identical to the insertion tool 200 discussed above, except as will hereinafter be discussed. More particularly, insertion tool 200A has its rod 210A formed so that a central bore 250A is formed therein. A movable rod 255A is slidably disposed within rod 210A, and the insertion tool's distal-most cylindrically-shaped portion 225A is attached to the distal end of movable rod 255A. As a result of this construction, the distal-most cylindrically-shaped portion 225A may be moved towards and away from the insertion tool's threaded portion 230A.

In use, movable rod 255A is first set in its projecting position, i.e., so that distal-most cylindrically-shaped portion 225A is separated from the insertion tool's threaded portion 230A (FIG. 33). With insertion tool 200A in this position, the insertion tool is screwed into bone cement plug 100. As this occurs, the rod's distal-most cylindrically-shaped portion 225A bottoms out on the bottom of the expander screw's bore 155 (FIG. 11), whereby the insertion tool will be prevented from advancing too far into expander screw 110 and thereby binding the insertion tool to the expander screw. In this respect it will also be appreciated that, to the extent that insertion tool advances sufficiently far into expander screw 110 as to begin to impart some stress to the union of the threads 156 and 230A, the insertion tool's distal-most cylindrically-shaped portion 230A will help take up such stress. Thereafter, when insertion tool 200A is to separate from bone cement plug 100, movable rod 255A is moved proximally so as to draw distal-most cylindrically-shaped portion 225A back towards threaded portion 230A (FIG. 34). This movement will release any residual stress which may exist between the insertion tool and the bone plug, whereby the insertion tool may easily separate from the bone cement plug.

Looking next at FIGS. 35–40, there is shown an alternative form of bone cement plug 500. Bone cement plug 500 is identical to the bone cement plug 100 discussed above, except as will hereinafter be discussed. More particularly, bone cement plug 500 has its base portion 515 formed so that its proximal portion 516 has an hexagonal cross-section.

Bone cement plug 500 is intended to be used in conjunction with the insertion tool 600 shown in FIGS. 41 and 42. Insertion tool 600 is identical to the insertion tool 200 discussed above, except as will hereinafter be discussed. More particularly, insertion tool 600 comprises a rod 610 which is identical to rod 210 described above. A handle 611 is fixed to the proximal end of rod 610. A sheath 612 is slidably and rotatably disposed about rod 610. Sheath 612 has a grip 613 fixed to its proximal end. The distal end of sheath 612 is arranged so as to have an hexagonal cross-section at 614 (FIG. 42) which corresponds to the hexagonal cross-section of the proximal portion 516 of bone cement plug 500.

As a result of this construction, it will be seen that sheath 612 may be slid proximally so as to expose the distal end of rod 610. Rod 610 may then be screwed into the bone cement plug's expander screw 510, whereby rod 610 will be rotatively joined to expander screw 510. Sheath 612 may then be slid distally, using grip 613, so as to cause the sheath's hexagonal section 614 to engulf (and thereby be rotatively coupled to) the bone cement plug's hexagonally-shaped proximal portion 516. Thereafter, bone cement plug 500 and insertion tool 600 may be used in the same manner previously described with respect to bone cement plug 100 and insertion tool 200, except that the positive connection between sheath 612 and bone cement plug 500 will permit the body of the bone cement plug to be held stationary against rotation within the bone canal as expander screw 510 is advanced into the core. Additionally, the positive connection between sheath 612 and bone cement plug 500 will also permit the bone cement plug to be easily turned in an arcuate fashion by sheath 612 while bone cement plug 500 is located within the distal end of the bone canal.

Looking next at FIGS. 43–48, there is shown an alternative form of bone cement plug 700. Bone cement plug 700 is identical to the bone cement plug 100 discussed above, except as will hereinafter be discussed. More particularly, bone cement plug 700 has its base portion 715 formed so that a plurality of slots 716 are formed therein.

Bone cement plug 700 is intended to be used in conjunction with the insertion tool 600A shown in FIG. 49. Insertion tool 600A is identical to the insertion tool 600 discussed above, except as will hereinafter be discussed. More particularly, insertion tool 600A comprises a sheath 612A which is slidably and rotatably disposed about rod 610. Sheath 612A has a grip 613 fixed to its proximal end. The distal end of sheath 612A is arranged so as to have a plurality of projections 614A which correspond to the slots 716 formed in the proximal portion 715 of bone cement plug 700.

As a result of this construction, it will be seen that sheath 612A may be slid proximally so as to expose the distal end of rod 610. Rod 610 may then be screwed into the bone cement plug's expander screw 710, whereby rod 610 will be rotatively joined to expander screw 710. Sheath 612A may then be slid distally, using grip 613, so as to cause the sheath's projections 614A to engage, and thereby to be rotatively coupled to, the bone cement plug's slots 716. Thereafter, bone cement plug 700 and insertion tool 600A may be used in the same manner previously described with respect to bone cement plug 100 and insertion tool 200, except that the positive connection between sheath 612A and bone cement plug 700 will permit the body of the bone cement plug to be held stationary against rotation within the bone canal as expander screw 710 is advanced into the core. Additionally, the positive connection between sheath 612A and bone cement plug 700 will also permit the bone cement plug to be easily turned in an arcuate fashion by sheath 612A while bone cement plug 700 is located within the distal end of the bone canal.

Looking next at FIGS. 50–55, there is shown an alternative form of bone cement plug 800. Bone cement plug 800 is identical to the bone cement plug 100 discussed above, except as will hereinafter be discussed. More particularly, bone cement plug 800 has its base portion 815 formed so that a set of screw threads 816 are formed thereon. The set of screw threads 816 is oriented in the opposite direction relative to the expander screw's external screw threads 160.

Bone cement plug 800 is intended to be used in conjunction with the insertion tool 600B shown in FIG. 56. Insertion tool 600B is identical to the insertion tool 600 discussed above, except as will hereinafter be discussed. More particularly, insertion tool 600B comprises a sheath 612B which is slidably and rotatably disposed about rod 610. Sheath 612B has a grip 613 fixed to its proximal end. The distal end of sheath 612B is arranged so as to have a set of screw threads 614B which corresponds to the set of screw threads 816 which are formed on the proximal portion 815 of bone cement plug 800.

As a result of this construction, it will be seen that sheath 612B may be slid proximally so as to expose the distal end of rod 610. Rod 610 may then be screwed into the bone cement plug's expander screw 810, whereby rod 610 will be rotatively joined to expander screw 810. Sheath 612B may then be slid distally and rotated, using grip 613, so as to cause the sheath's set of screw threads 614B to engage, and thereby to be rotatively coupled to, the bone cement plug's set of screw threads 816. Thereafter, bone cement plug 800 and insertion tool 600B may be used in the same manner previously described with respect to bone cement plug 100 and insertion tool 200, except that the positive connection between sheath 612B and bone cement plug 800 will permit the body of the bone cement plug to be held stationary against rotation within the bone canal as expander screw 810 is advanced into the core. Additionally, the positive connection between sheath 612B and bone cement plug 800 will also permit the bone cement plug to be easily turned in an arcuate fashion by sheath 612B while bone cement plug 800 is located within the distal end of the bone canal.

It should also be appreciated that, while in the foregoing discussion core 105 has been described and shown to have two opposing legs 130, 135, more than two legs could also be provided.

It will be appreciated that the principles and features of the present invention may be employed in various and numerous embodiments without departing from the scope of the present invention. Thus, it will be understood that the present invention is by no means limited to the particular construction herein disclosed and/or shown in the drawings, but also comprises any modifications or equivalents within the scope of the claims.

Advantages Of The Invention

Numerous advantages are achieved through the provision and use of the present invention.

For one thing, the present invention provides a bone cement plug which improves upon the bone cement plugs previously known in the art.

For another thing, the present invention provides an improved bone cement plug which is easy to deploy at the distal end of the bone canal, effective in closing off that bone canal and, in the event that the bone cement plug subsequently needs to be removed, easy to retrieve from the distal end of the bone canal.

And the present invention provides a bone cement plug which is bio-compatible with the patient, and which is inexpensive to produce.

Also, the present invention provides an insertion tool for deploying the bone cement plug at the distal end of the bone canal and, in the event that the bone cement plug subsequently needs to be removed, an extraction tool for retrieving the bone cement plug from the distal end of the bone canal.

Furthermore, the present invention provides an improved method for closing off the distal end of a bone canal.

What is claimed is:

1. A core for forming a bone cement plug for deployment in a bone canal having an internal wall defining an inside diameter, said core comprising:

a substantially cylindrically-shaped base portion defining a threaded bore therein extending axially and distally from a proximal end of said base portion;

a first leg portion depending from and extending distally from said base portion;

a second leg portion depending from and extending distally from said base portion and opposed to said first leg portion; and a plurality of annular flanges extending outwardly from said core and engageable with a wall of the bone canal, said flanges being flexible, a proximal-most of said flange having a diameter exceeding the bone canal diameter, such that said proximal-most flange is adapted to be compressed by the wall of the bone canal, and wherein peripheral portions of said proximal-most flange override adjacent peripheral portions of said proximal-most flange;

said base portion threaded bore being adapted to receive an expander screw to wedge apart said first and second leg portions, whereby to expand said core widthwise to secure said core in the bone canal.

2. A core according to claim 1 wherein said leg portions prior to expansion abut each other and together form a substantially cylindrical configuration of substantially the same diameter as a diameter of said base portion.

3. A core according to claim 2 wherein said leg portions after said expansion are separated from each other and extend from the base portion in diametrically opposed outwardly directions to assume a generally oval configuration in the bone canal.

4. A core according to claim 1 wherein said base portion and said leg portions define therebetween an annular groove.

5. A core according to claim 4 wherein said annular groove is provided with a slit extending widthwise through said plug, said slit extending through proximal and substantially equal portions of said first and second legs.

6. A core according to claim 1 wherein said base portion and said leg portions define therebetween a slit extending widthwise through said core, said slit extending through proximal and substantially equal portions of said first and second legs.

7. A core according to claim 1 wherein said core is of a material selected from a group of materials consisting of metal, plastic, bioabsorbable material, and metal-plastic composites.

8. A core according to claim 7 wherein said plastic consists of a selected one of polyethylene and polypropylene.

9. A core for forming a bone cement plug for deployment in a bone canal, said core comprising:

a substantially cylindrically-shaped base portion defining a threaded bore therein extending axially and distally from a proximal end of said base portion;

a first leg portion depending from and extending distally from said base portion;

a second leg portion depending from and extending distally from said base portion and opposed to said first leg portion; and a plurality of annular flanges extending outwardly from said core and engageable with a wall of the bone canal, said flanges being flexible;

said base portion threaded bore being adapted to receive an expander screw to wedge apart said first and second leg portions, whereby to expand said core widthwise to secure said core in the bone canal;

wherein a proximal-most flange of said plurality of flanges is provided with a plurality of slits extending radially inwardly from a periphery of said proximal-most flange toward an inner edge of said proximal-most flange to a point spaced from said inner edge of said proximal-most flange.

10. A core according to claim 9 wherein each of said slits extends through said proximal-most flange at an angle to a lengthwise axis of said core.

11. A core according to claim 10 wherein said angle is about 30°–60°.

12. A core according to claim 11 wherein said angle is about 45°.

13. A core according to claim 9 wherein said proximal-most flange is provided with a diameter exceeding a diameter of the bone canal, such that said proximal-most flange is compressed by the wall of the bone canal, and said slits permit portions of said proximal-most flange each to override an adjacent portion of said proximal-most flange.

14. A core according to claim 1 wherein said proximal-most flange of said plurality of flanges extends from said base portion, and a distal-most flange of said plurality of flanges includes a first portion extending from said first leg and a second portion extending from said second leg.

15. A bone cement plug comprising:
a core comprising:
a substantially cylindrically-shaped base portion defining a threaded bore therein extending axially and distally from a proximal end of said base portion;
a first leg portion depending from and extending distally from said base portion; and
a second leg portion depending from and extending distally from said base portion and opposed to said first leg portion;
said base portion threaded bore being adapted to receive an expander screw to wedge apart said first and second leg portions, whereby to expand said core widthwise to secure said plug in the bone canal;
said expander screw, said screw comprising:
a generally cylindrically-shaped body having a tapered distal end, and a proximal end in which is disposed a threaded bore, external threads disposed on said body, and an annular flange extending outwardly from said proximal end of said body, said screw being threadedly engageable with said core threaded bore for advancement of said screw into said plug for said wedging apart of said first and second legs;
wherein said screw threaded bore is provided with first and second sets of threads, said first set of threads being adapted to receive a screw insertion tool, and said second set of threads being adapted to receive a screw extraction tool; and
insertion tool comprising:
a rod having at a distal end thereof a tip portion of reduced diameter, said tip portion including a distal-most cylindrically-shaped portion adapted to be non-threadedly received by said screw second set of threads, and a proximal-most threaded portion adapted to be threadedly received by said screw first set of threads, whereby said tool is adapted to advance said screw into said plug.

16. A bone cement plug according to claim 15 wherein said second set of threads is in axial alignment with said first set of threads, is of smaller diameter than said first set of threads, and is disposed distally of said first set of threads.

17. A bone cement plug according to claim 15 wherein said second set of threads extend in an opposite direction relative to said first set of threads.

18. A bone cement plug according to claim 15 wherein said first set of threads extend in the same direction as said external threads disposed on said body of said expander screw.

19. A bone cement plug according to claim 15 wherein said rod at a juncture with said tip portion is provided with an annular shoulder for engagement with said screw annular flange.

20. A bone cement plug according to claim 19 wherein said annular shoulder is provided with ratchet teeth and said screw annular flange is provided with complementary ratchet teeth, such that engagement of said shoulder and flange ratchet teeth cause turning of said rod to cause turning of said screw.

21. A bone cement plug according to claim 15 wherein said distal-most cylindrically-shaped portion is movable towards and away from said proximal-most threaded portion.

22. A bone cement plug according to claim 15 wherein said insertion tool rod is provided with means thereon for engagement with said plug base portion, and said plug base portion is provided with means thereon for engagement with said rod engagement means, such that said rod engagement means is adapted to engage said plug engagement means and prevent said plug from rotating while said rod proximal-most threaded portion is threadedly received by said screw first set of threads to advance said screw in said plug.

23. A bone cement plug according to claim 22 wherein said rod includes a sleeve portion defining an axial bore therethrough, and a spindle portion movably disposed in said rod sleeve portion, said proximal-most threaded portion being disposed on said rod spindle portion and said means for engagement with said plug being disposed on said rod sleeve portion.

24. A bone cement plug to claim 23 wherein said means for engagement with said plug comprises an internal distal end portion of said sleeve complementarily configured relative to said plug base portion.

25. A bone cement plug according to claim 22 wherein said means for engagement with said plug comprises pins extending distally from a distal end of said rod sleeve and said means on said plug for engaging said rod comprises holes for receiving said pins.

26. A bone cement plug according to claim 22 wherein said means for engagement with said plug comprises internal threads on a distal end of said sleeve portion, and a straight-sided projection extending distally from said rod spindle portion, and said means on said plug for engagement with said rod comprises external threads on said plug base portion, said screw having an axial recess therein extending distally from a proximal end of said screw and adapted to receive said rod spindle projection.

27. A bone cement plug according to claim 15 wherein said first and second legs cooperatively define a tapered bore portion complementary to said screw tapered distal end.

28. A bone cement plug comprising:
a core comprising:
a substantially cylindrically-shaped base portion defining a threaded bore therein extending axially and distally from a proximal end of said base portion;
a first leg portion depending from and extending distally from said base portion; and
a second leg portion depending from and extending distally from said base portion and opposed to said first leg portion;
said base portion threaded bore being adapted to receive an expander screw to wedge apart said first and second leg portions, whereby to expand said core widthwise to secure said plug in the bone canal;
said expander screw, said screw comprising:
a generally cylindrically-shaped body having a tapered distal end, and a proximal end in which is disposed a threaded bore, external threads disposed on said body, and an annular flange extending outwardly from said proximal end of said body, said screw being threadedly engageable with said core threaded bore for advancement of said screw into said plug for said wedging apart of said first and second legs;

wherein said screw threaded bore is provided with first and second sets of threads, said first set of threads being adapted to receive a screw insertion tool, and said second set of threads being adapted to receive a screw extraction tool;

said extraction tool comprising a rod having at a distal end thereof a tip portion of reduced diameter, said tip portion including a distal-most threaded portion adapted to be threadedly received by said screw second set of threads, and a proximal-most cylindrically-shaped portion adapted to be non-threadedly received by said screw first set of threads, whereby said tool is adapted to withdraw said screw from said plug; and a sizer ball for removable mounting on said extraction tool tip portion.

29. A bone cement plug in accordance with claim 28 wherein another sizer ball is disposed on the proximal end of said rod.

30. A method for fixing a bone cement plug in a bone canal, the method comprising the steps of:

providing a bone cement plug comprising:

a bone cement plug for deployment in a bone canal, said bone cement plug comprising:

a substantially cylindrically-shaped base portion defining a threaded bore therein extending axially and distally from a proximal end of said base portion;

a first leg portion depending from and extending distally from said base portion; and a second leg portion depending from and extending distally from said base portion and opposed to said first leg portion;

said base portion threaded bore being adapted to receive an expander screw to wedge apart said first and second leg portions, whereby to expand said plug widthwise to secure said plug in the bone canal; and a plurality of annular flanges extending outwardly from said plug and engageable with a wall of said bone canal; and said expander screw, said screw comprising:

a generally cylindrically-shaped body having a tapered distal end and a proximal end in which is disposed a threaded bore, external threads disposed on said body, and an annular flange extending outwardly from said proximal end of said body, said screw being threadedly engageable with said plug threaded bore for advancement of said screw into said plug for said wedging apart of said first and second legs;

advancing said plug into the bone canal with at least one of said flanges engaging the wall of the bone canal; and advancing said screw in said plug to effect said expansion of said plug widthwise in the bone canal.

31. A method according to claim 30 including the step prior to advancing the plug into the bone canal of advancing said screw in said plug sufficiently to partially expand said plug such that at least one of said annular flanges engage the wall of the bone canal upon insertion of said plug into the bone canal.

32. A method according to claim 30 including the additional steps of fully expanding said plug in the bone canal, and rotating said plug in the bone canal to move said legs into engagement with portions of the canal wall closer together than most spaced-apart portions thereof.

* * * * *